United States Patent
Leaders et al.

(10) Patent No.: US 10,281,437 B2
(45) Date of Patent: May 7, 2019

(54) ULTRASONIC SENSOR ASSEMBLY FOR FLUID FLOW METERS

(71) Applicant: Soneter Inc., Atlanta, GA (US)

(72) Inventors: Jeffrey L. Leaders, Atlanta, GA (US); Francis M. Mess, Smyrna, GA (US); Clayton C. Pumphrey, Duluth, GA (US); Jorge C. Almirall, Acworth, GA (US)

(73) Assignee: Reliance Worldwide Corporation, Atlanta, GA (US)

( * ) Notice: Subject to any disclaimer, the term of this patent is extended or adjusted under 35 U.S.C. 154(b) by 183 days.

(21) Appl. No.: 15/317,358

(22) PCT Filed: Jun. 10, 2015

(86) PCT No.: PCT/US2015/035196
§ 371 (c)(1),
(2) Date: Dec. 8, 2016

(87) PCT Pub. No.: WO2015/191775
PCT Pub. Date: Dec. 17, 2015

(65) Prior Publication Data
US 2017/0122916 A1    May 4, 2017

Related U.S. Application Data

(60) Provisional application No. 62/010,197, filed on Jun. 10, 2014.

(51) Int. Cl.
*G01F 1/66* (2006.01)
*G01N 29/32* (2006.01)
(Continued)

(52) U.S. Cl.
CPC .......... *G01N 29/326* (2013.01); *G01F 1/662* (2013.01); *G01N 29/02* (2013.01); *G01N 29/024* (2013.01);
(Continued)

(58) Field of Classification Search
None
See application file for complete search history.

(56) References Cited

U.S. PATENT DOCUMENTS 5,001,936 A    3/1991  Baumoel
5,179,862 A *  1/1993  Lynnworth ............ G01F 1/662
                                                        73/861.28
(Continued)

OTHER PUBLICATIONS

International Search Report and Written Opinion regarding PCT/US2015/35196 dated Sep. 18, 2015.
(Continued)

*Primary Examiner* — Harshad R Patel
(74) *Attorney, Agent, or Firm* — Foley & Lardner LLP

(57) ABSTRACT

A sensor assembly is configured to mount transducers on a conduit, such as a pipe, for measuring properties of a fluid flowing in the conduit. The sensor assembly can include a sensor cradle capable of seating and maintaining a pair of transducers. The sensor assembly can include a mounting device arranged to couple the sensor cradle to the conduit such that the transducers maintained at the sensor cradle are oriented to allow transmission of ultrasonic waves traversing the conduit. The sensor assembly allows for mechanically stable coupling of the transducers to the conduit. The transducers can be fixed to the sensor cradle though an adhesive. In some implementations, the transducers can be oriented substantially orthogonal to each other.

22 Claims, 45 Drawing Sheets

(51) Int. Cl.
*G01N 29/024* (2006.01)
*G01N 29/22* (2006.01)
*G01N 29/02* (2006.01)
*G01N 29/26* (2006.01)

(52) U.S. Cl.
CPC ......... *G01N 29/221* (2013.01); *G01N 29/222* (2013.01); *G01N 29/26* (2013.01); *G01N 2291/0423* (2013.01); *G01N 2291/102* (2013.01); *G01N 2291/2634* (2013.01)

(56) References Cited

U.S. PATENT DOCUMENTS

| | | | | |
|---|---|---|---|---|
| 6,047,602 | A * | 4/2000 | Lynnworth | G01F 1/662 73/632 |
| 6,883,386 | B2 * | 4/2005 | Osone | G01F 1/662 73/861.25 |
| 7,146,846 | B2 | 12/2006 | Mahaffey et al. | |
| 7,146,864 | B2 * | 12/2006 | Sullivan | G01F 1/662 73/861.42 |
| 8,186,229 | B2 * | 5/2012 | Allen | G01F 1/662 73/861.18 |
| 8,544,342 | B1 | 10/2013 | Feller | G01F 1/3218 73/861.24 |
| 8,833,157 | B2 * | 9/2014 | Bremigan, III | G01F 23/2961 73/290 V |
| 8,919,208 | B2 * | 12/2014 | Murakami | G01F 1/667 73/861.27 |
| 9,146,172 | B2 * | 9/2015 | Trescott | G01M 3/002 |
| 2003/0172743 | A1 | 9/2003 | Ao et al. | |
| 2004/0011141 | A1 * | 1/2004 | Lynnworth | G01F 1/662 73/861.27 |
| 2004/0123666 | A1 * | 7/2004 | Ao | G01F 1/662 73/644 |
| 2004/0173029 | A1 | 9/2004 | Osone et al. | |
| 2007/0186681 | A1 * | 8/2007 | Shkarlet | A61B 5/6876 73/861.28 |
| 2008/0236296 | A1 * | 10/2008 | Sonnenberg | G01F 1/74 73/861.26 |
| 2010/0307263 | A1 | 12/2010 | Gysling et al. | |
| 2011/0162463 | A1 | 7/2011 | Allen | |
| 2012/0031199 | A1 | 2/2012 | Bremigan et al. | |
| 2012/0180877 | A1 | 7/2012 | Pallais | |
| 2012/0318069 | A1 | 12/2012 | Murakami | |

OTHER PUBLICATIONS

Supplementary European Search Report for EP 15806392.5 dated Feb. 21, 2018.
Supplementary Partial European Search Report for EP Application No. 15806392 dated Oct. 20, 2017.
Examination Search Report for Canada Application No. 2,952,064 dated Oct. 6, 2017. (4 pages).
International Preliminary Report on Patentability for PCT/US2015/035196 dated Dec. 22, 2016.
Examination Search Report for CA Application No. 2,952,064 dated Sep. 5, 2018.

* cited by examiner

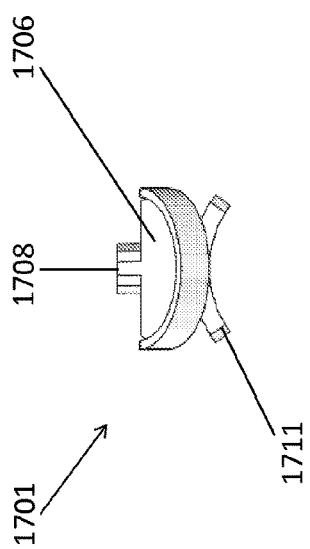
Figure 17A
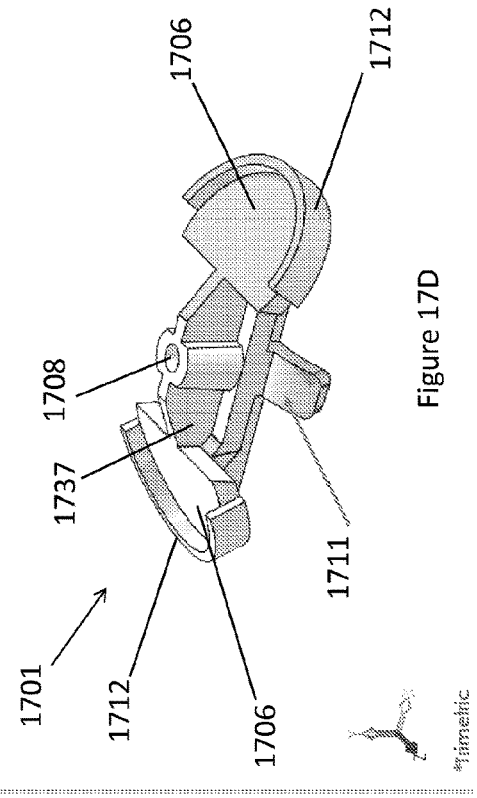
Figure 17B
Figure 17D
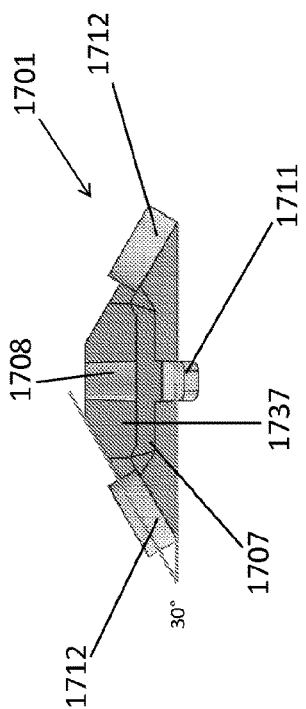
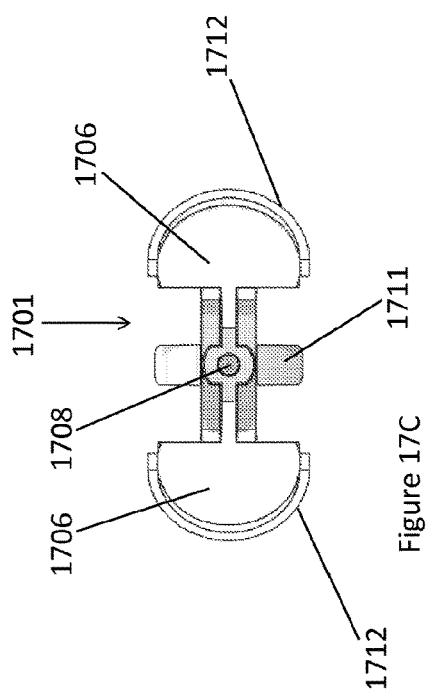
Figure 17C

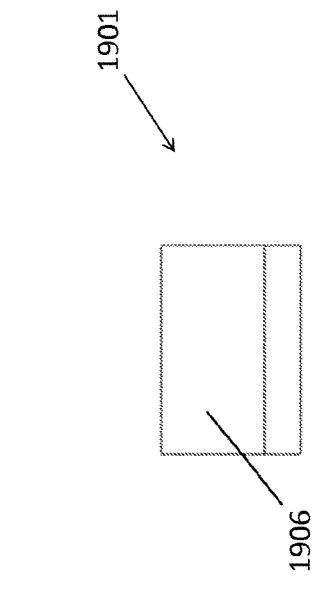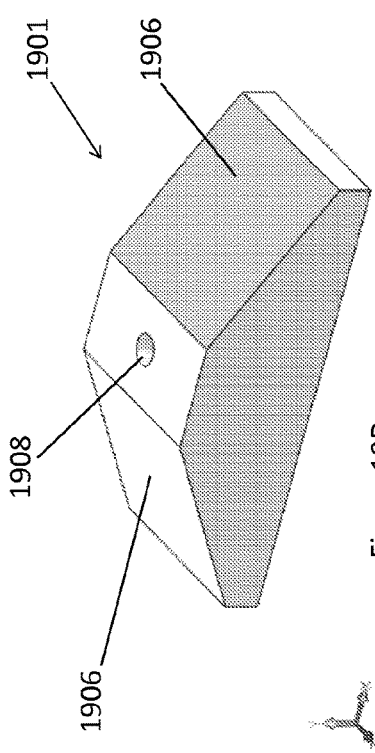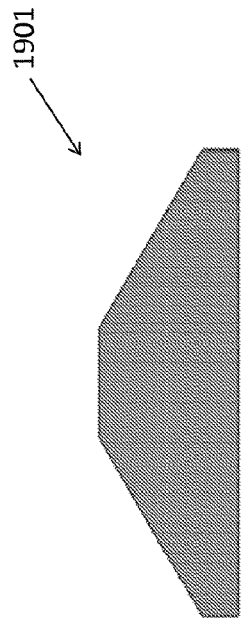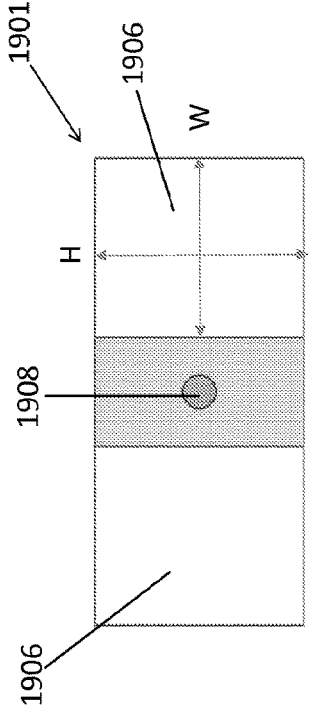

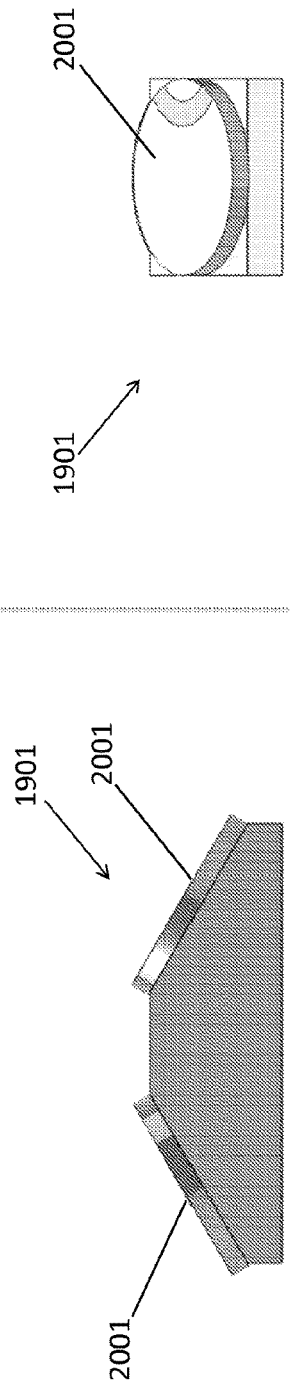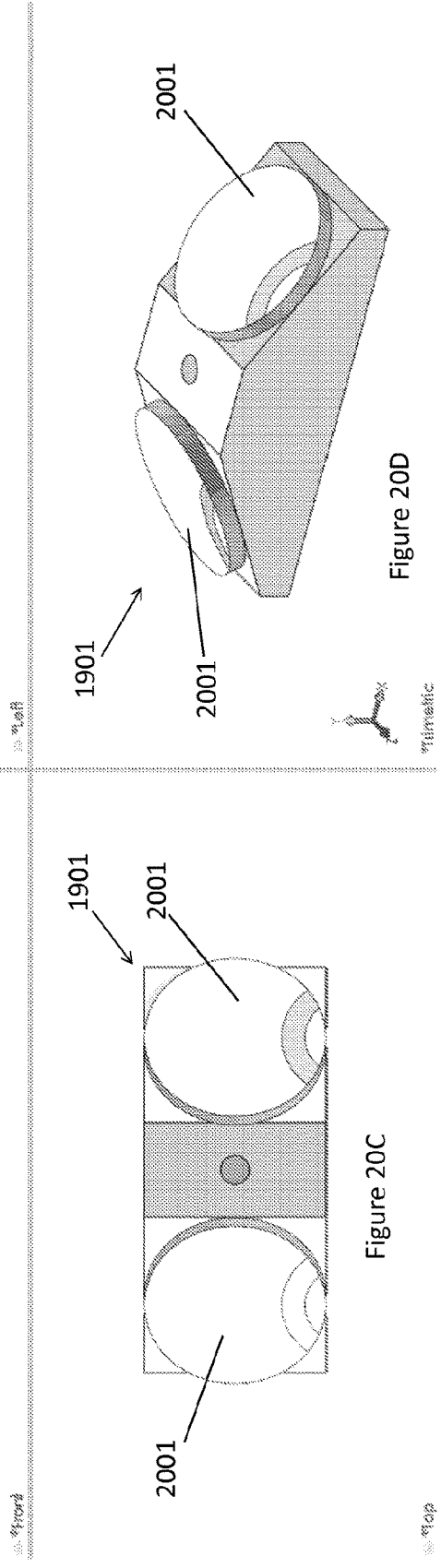

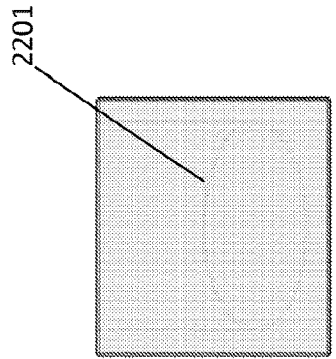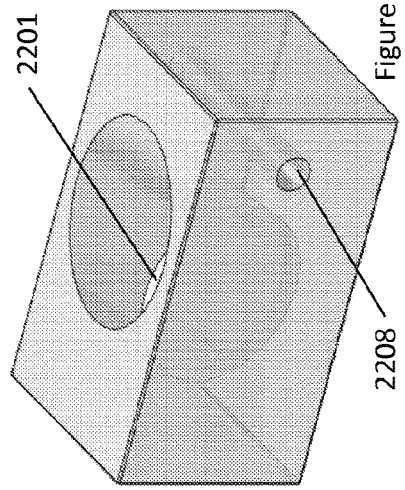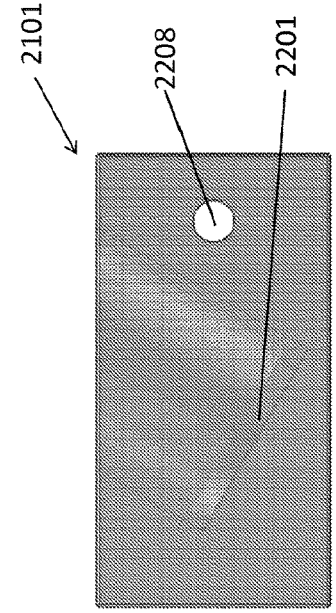
Figure 22A
Figure 22B
Figure 22C
Figure 22D

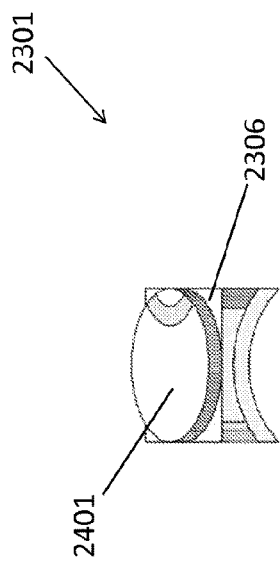
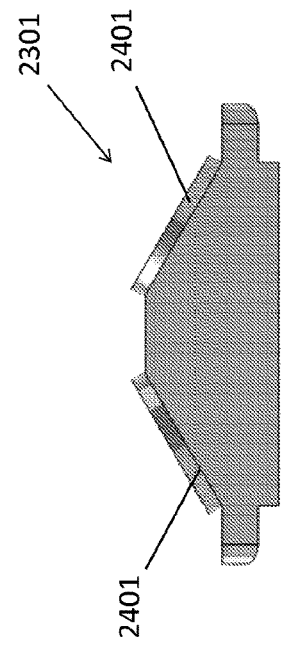
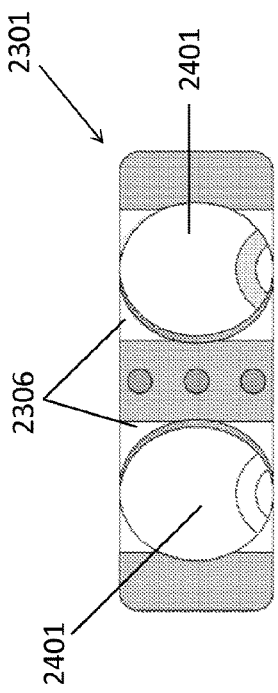
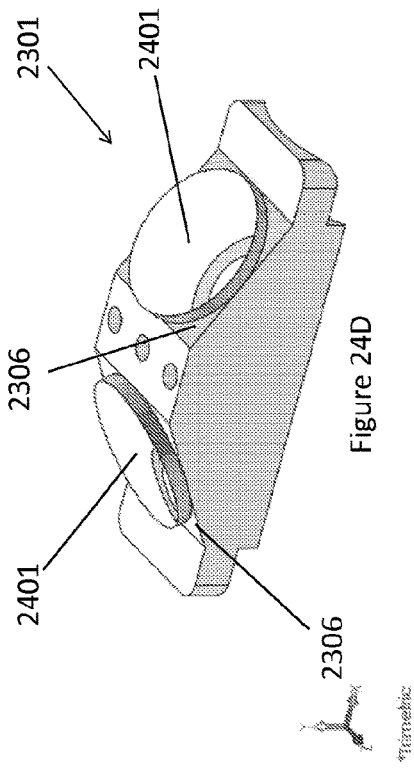
Figure 24A
Figure 24B
Figure 24C
Figure 24D

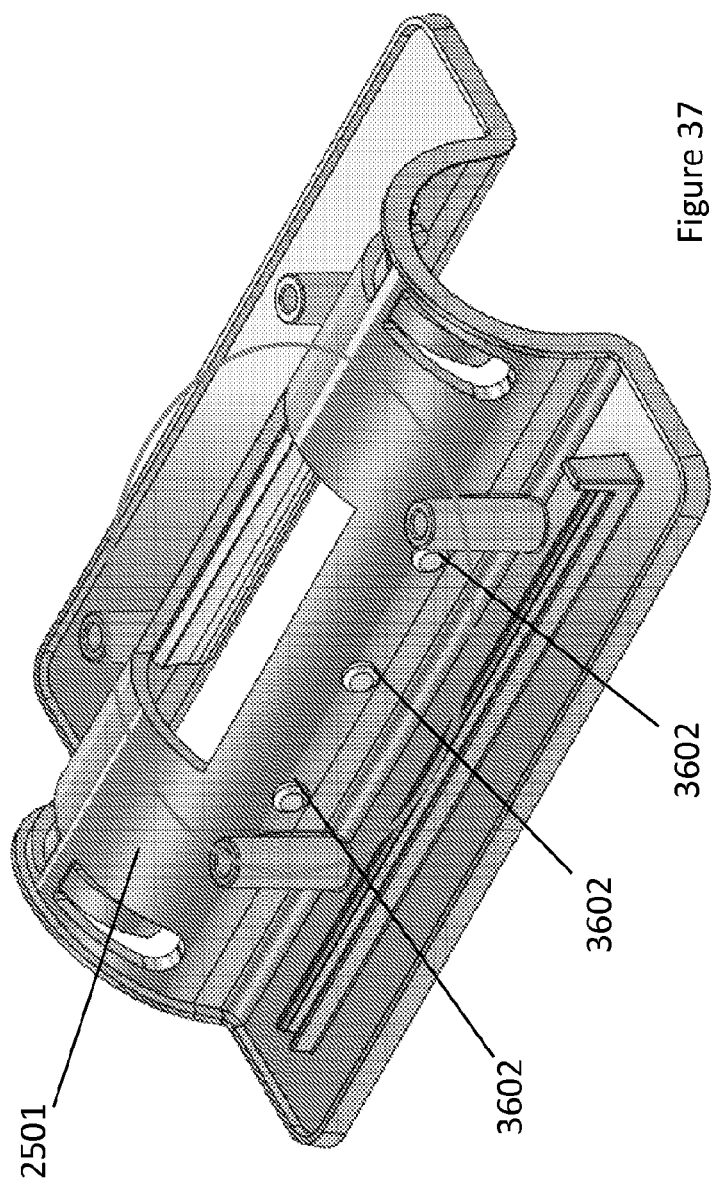

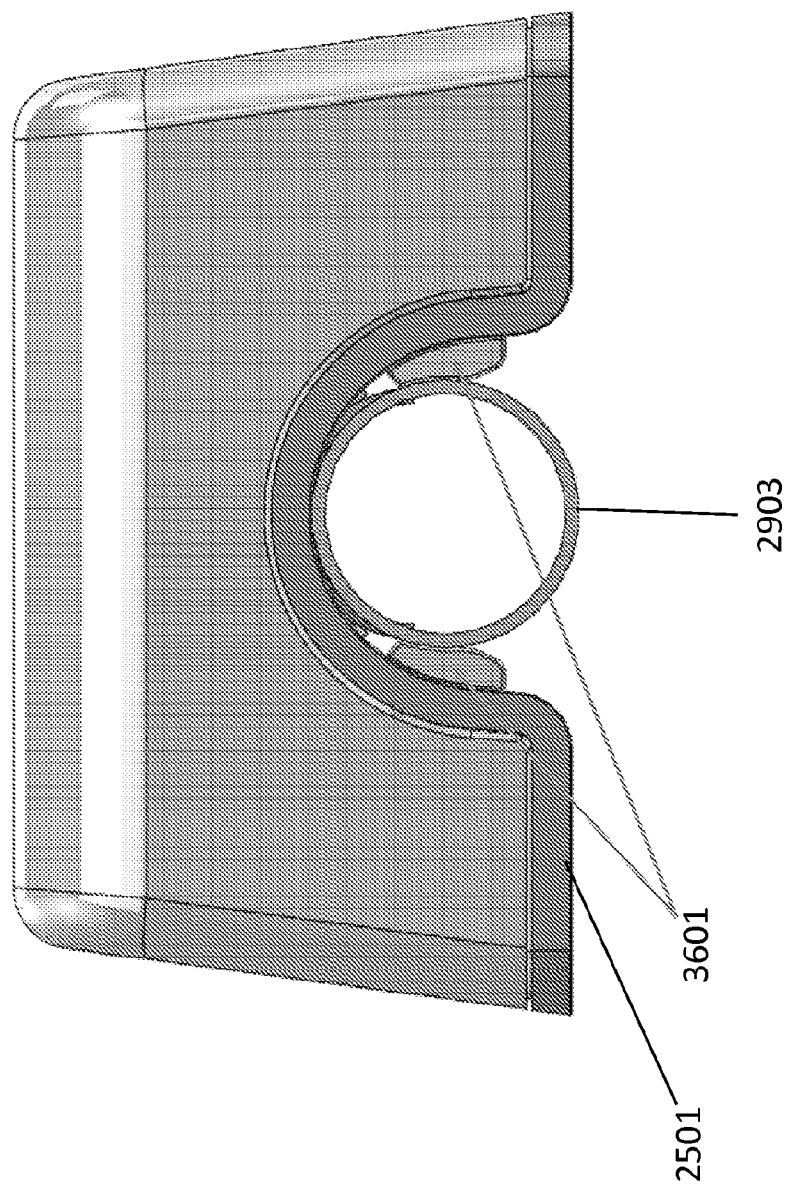

ULTRASONIC SENSOR ASSEMBLY FOR FLUID FLOW METERS

RELATED APPLICATION

This application is a U.S. National Stage of International Application No. PCT/US2015/035196, titled "Sensor Assembly" filed on Jun. 10, 2015, which in turn claims priority to U.S. Patent Provisional Patent Application No. 62/010,197, titled "Sensor Assembly" filed on Jun. 10, 2014, contents of all of which are incorporated herein.

TECHNICAL FIELD

The present application relates generally to detection of various properties associated with a fluid flowing within a conduit such as a pipe and related components associated with the detection therein.

SUMMARY

Various embodiments provide a detection assembly for detecting various fluid properties and related components and methods of manufacturing and implementing a detection assembly and related components for detecting various fluid properties.

A sensor assembly is configured to mount transducers on a conduit for measuring properties of a fluid flowing in the conduit. The sensor assembly can include a sensor cradle capable of seating and maintaining a pair of transducers. The sensor assembly can include a mounting device arranged to couple the sensor cradle to the conduit such that the transducers maintained at the sensor cradle are oriented to allow transmission of ultrasonic waves traversing the conduit. The transducers can be fixed to the sensor cradle though an adhesive. In some implementations, the transducers can be oriented substantially orthogonal to each other. The transducers can be seated within recessed mounting surfaces or within openings of the of the sensor cradle.

BRIEF DESCRIPTION OF THE DRAWINGS

The skilled artisan will understand that the drawings primarily are for illustrative purposes and are not intended to limit the scope of the subject matter described herein. The drawings are not necessarily to scale; in some instances, various aspects of the subject matter disclosed herein may be shown exaggerated or enlarged in the drawings to facilitate an understanding of different features. In the drawings, like reference characters generally refer to like features (e.g., functionally similar and/or structurally similar elements).

FIGS. 17A-17D illustrate another sensor cradle including dual wave-guides and configured for disposition within a housing guide in accordance with example implementations.

FIGS. 19A-19D illustrate a trapezoidal sensor cradle in accordance with exemplary embodiments.

FIGS. 20A-20D illustrate the trapezoidal sensor cradle of FIGS. 19A-19D having transducers coupled thereto in accordance with example implementations.

FIGS. 22A-22D illustrate the trapezoidal sensor cradle of FIGS. 21A-21D having a transducer coupled thereto in accordance with exemplary embodiments.

FIGS. 24A-24D illustrate the trapezoidal sensor cradle of FIGS. 23A-23D having transducers coupled thereto in accordance with example implementations.

FIG. 37 shows the wedge of FIG. 36 coupled to a mounting portion in accordance with example implementations.

FIG. 38 provides an end view of a sensor cradle housing assembly coupled to a pipe in accordance with example implementations.

The features and advantages of the inventive concepts disclosed herein will become more apparent from the detailed description set forth below when taken in conjunction with the drawings.

DETAILED DESCRIPTION

Following below are more detailed descriptions of various concepts related to, and embodiments of, inventive systems, and methods of forming an sensor cradle. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

Figure 1:
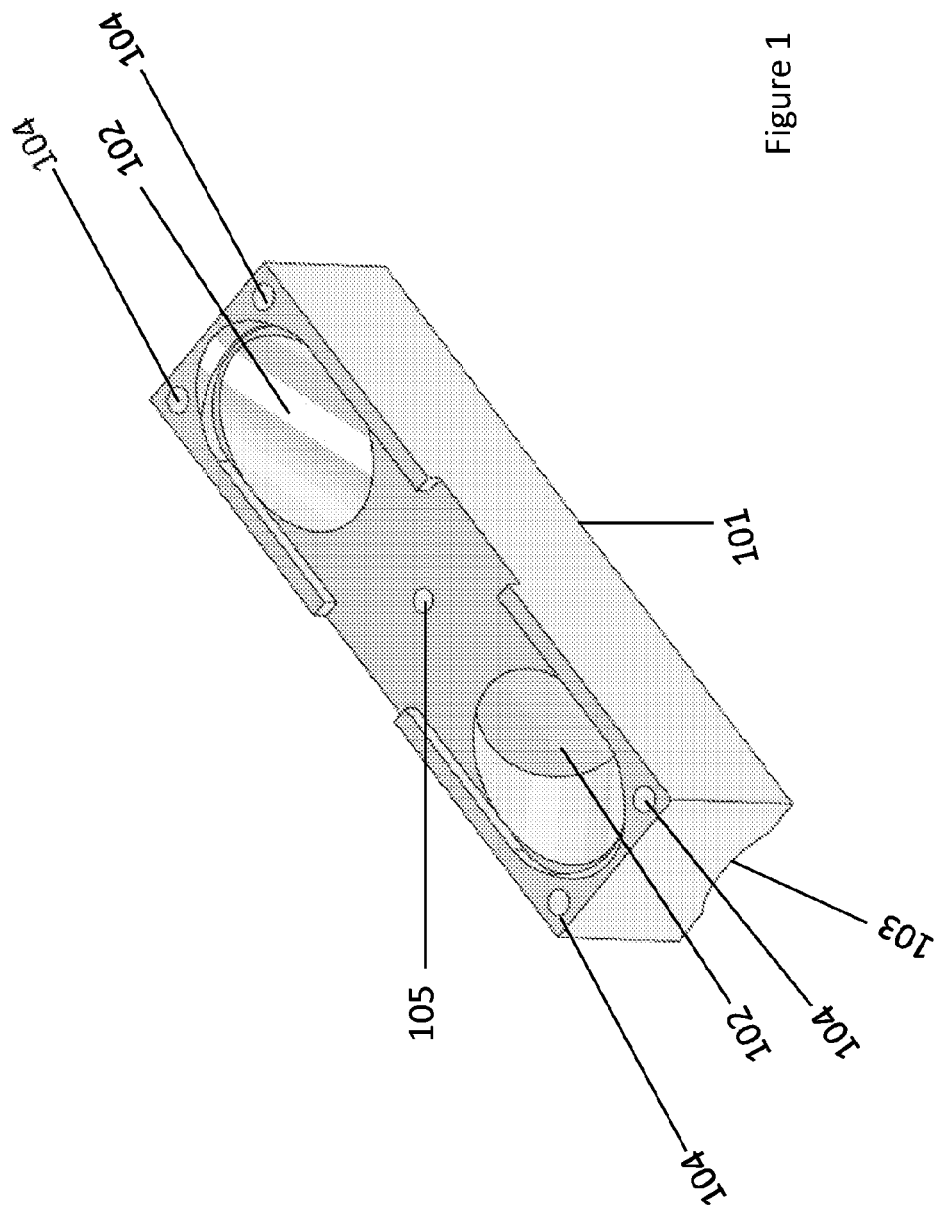
FIG. 1 provides a perspective view of a sensor cradle in accordance with example implementations.

FIG. 1 provides a perspective view of a sensor cradle in accordance with example implementations. The sensor cradle 101 illustrated in FIG. 1 is provided in a block-like form. The sensor cradle 101 includes two transducer openings 102 for seating and maintaining transducers, such as ultrasonic transducers, for measuring properties of fluid flowing in the wave path of the transducers. The transducer openings 102 are configured to orient the transducers for wave transmission traversing a pipe positioned adjacent to the cradle. In the illustrated implementation, the transducer openings 102 are configured to orient transducers or flow meters positioned therein such that the transducers will transmit waves substantially orthogonal with respect to one another. The sensor cradle 101 includes a curved interface 103 configured for engaging the sensor cradle 101 with a conduit such as a pipe for transferring fluids, such as water or gas. In accordance with example implementations, transducers disposed in the transducer openings 102 can be configured to measure fluid properties including, but not limited to, fluid flow rate and fluid temperatures.

In accordance with example implementations, transducers disposed in the transducer openings 102 can be configured to compensate for the temperature of the fluid. More specifically, two signals namely an "upstream" signal and a "downstream" signal may be used to compensate for variations in the measurement of transducers disposed in the sensor cradle 101 due to changes in speed of sound as a function of temperature. By using upstream and downstream measurements, the average time of flight is related to temperature, and the differential time of flight (e.g. upstream minus downstream) is due to flow. However, asymmetry in the flight path can lead to variation in the differential time of flight as a function of temperature. The average time of flight can be used to compensate for this temperature-driven asymmetry. In some implementations, the angle of orientation of the transducer openings 102 may be configured in accordance with properties of a particular pipe, such as pipe material and pipe geometry, to optimize signal propagation and strength. The sensor cradle 101 may also include a plurality of fastener openings 104, which may be used to fasten an outer shroud or covering to the sensor cradle 101. The sensor cradle 101 may also include one or more bore holes 105 configured and positioned for housing an auxiliary component such as a thermistor or another type of sensor in accordance with example implementations.

Sensor cradle 101 may be produced by machining in accordance with exemplary embodiments and may be composed of materials such as acrylic, polycarbonate, polysulfone, and other plastics with appropriate mechanical and signal transmission properties. The sensor cradle may also be composed of metals such as aluminum or copper depending on the requirements of a given application. In some implementations, the sensor cradle may be composed of more than one material. For example the body of the cradle 101 may be composed of a first material and the curved interface 103 may be composed in whole or in part of a distinct material. In some implementations, sensor cradle 101 may be configured with transducers positioned in the sensor cradle 101 at or between 0°-85° with respect to an axis perpendicular to the curved pipe interface 103 and/or the pipe wall coupled to the sensor cradle 101. It will be appreciated that although still able to measure other fluid properties, sensitivity to flow is decreased at smaller angles, with the transmitted signal being insensitive to flow at 0°. Depending on the type of signal being used for fluid interrogation (e.g. transverse versus Rayleigh waves) different launch angles may be used to preferentially couple signal into the pipe wall, the fluid, or both.

Figure 2:
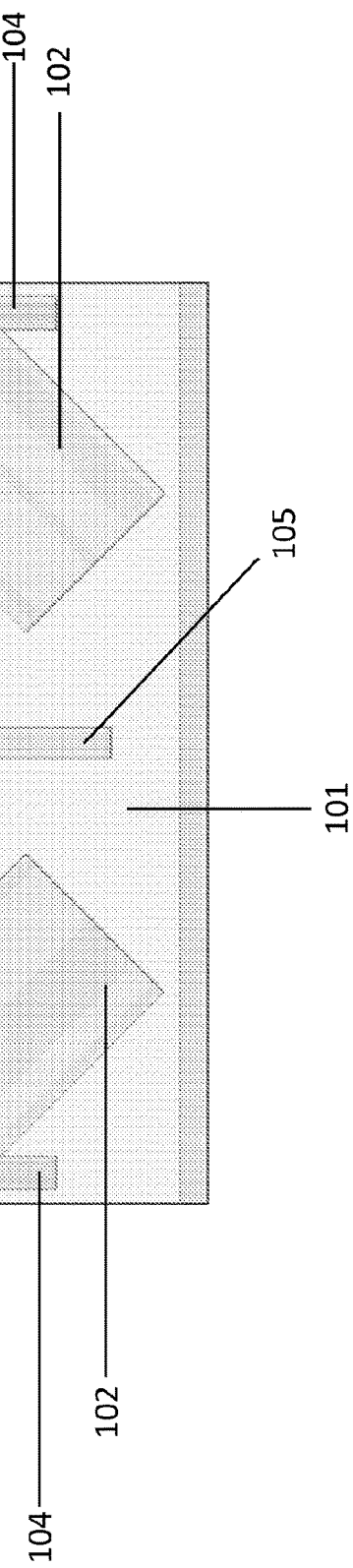
FIG. 2 is side view of the sensor cradle of FIG. 1.

FIG. 2 shows a side view of the sensor cradle of FIG. 1. As shown in FIG. 2, the transducer openings 102 may not extend completely through the body of the sensor cradle 101. In accordance with example implementations, the sensor cradle 101 may receive waves, such as ultrasonic waves transmitted by transducers disposed within the transducer openings 102 for calibration of a meter, sensor, or detection unit coupled to the transducers. The time of flight of the signal transmitted between the transducers is related to the speed of the signal along the transmission path. The signal propagation speed can vary as a function of temperature. Since the cradle geometry is fixed, the average time of flight between the two transducers can be used to measure the temperature of the fluid. As noted herein, the transducer openings 102 can be positioned substantially orthogonal to one another (such as at an angle between 80°-90°). Transducer openings 102 provide a passive alignment mechanism for the transducer's disposed therein. The transducer openings 102 may be positioned at other angular configurations with respect to one another in accordance with example implementations. The angular configuration and the distance between the transducer openings may be selected to optimize the signal strength and propagation path for a given pipe material composition and diameter 103. The angular configuration and the distance between the transducer openings may be altered based on the material composition of the body of the sensor cradle 101 and of the pipe, and based on the diameter of the pipe. The cradle material, angular configuration, the distance between the transducer openings, and the transducer characteristics (size and signal emission profile) can be selected to allow a single sensor cradle to function on a combination of different pipe diameters and materials.

As also shown in FIG. 2, bore hole 105 may be positioned close to the path of projection of the signal or waves from transducers disposed in the transducer openings 102 without actually being in the projected propagation path, which position may be substantially central in the block to best approximate the thermal distribution in the body of the sensor cradle 101 experienced by the sensor signal during propagation through the cradle. Information provided by signals produced from a thermistor disposed in bore hole 105 may be used to provide the temperature component of a speed of sound calculation through the body of sensor cradle 101. In accordance with example implementations, sensor cradle 201 may be configured with transducers positioned in the sensor cradle 201 at or between 0°-85° with respect to an axis perpendicular to the mounting portion 203 and/or the pipe wall coupled to the sensor cradle. In accordance with example implementations, sensor cradle 201 may be composed of a combination of one or more metals (including but not limited to aluminum or copper) and polymers (including but not limited to plastics such as acrylic, polycarbonate, polysulfone, polystyrene, nylon, and polypropylene.

Figure 3:
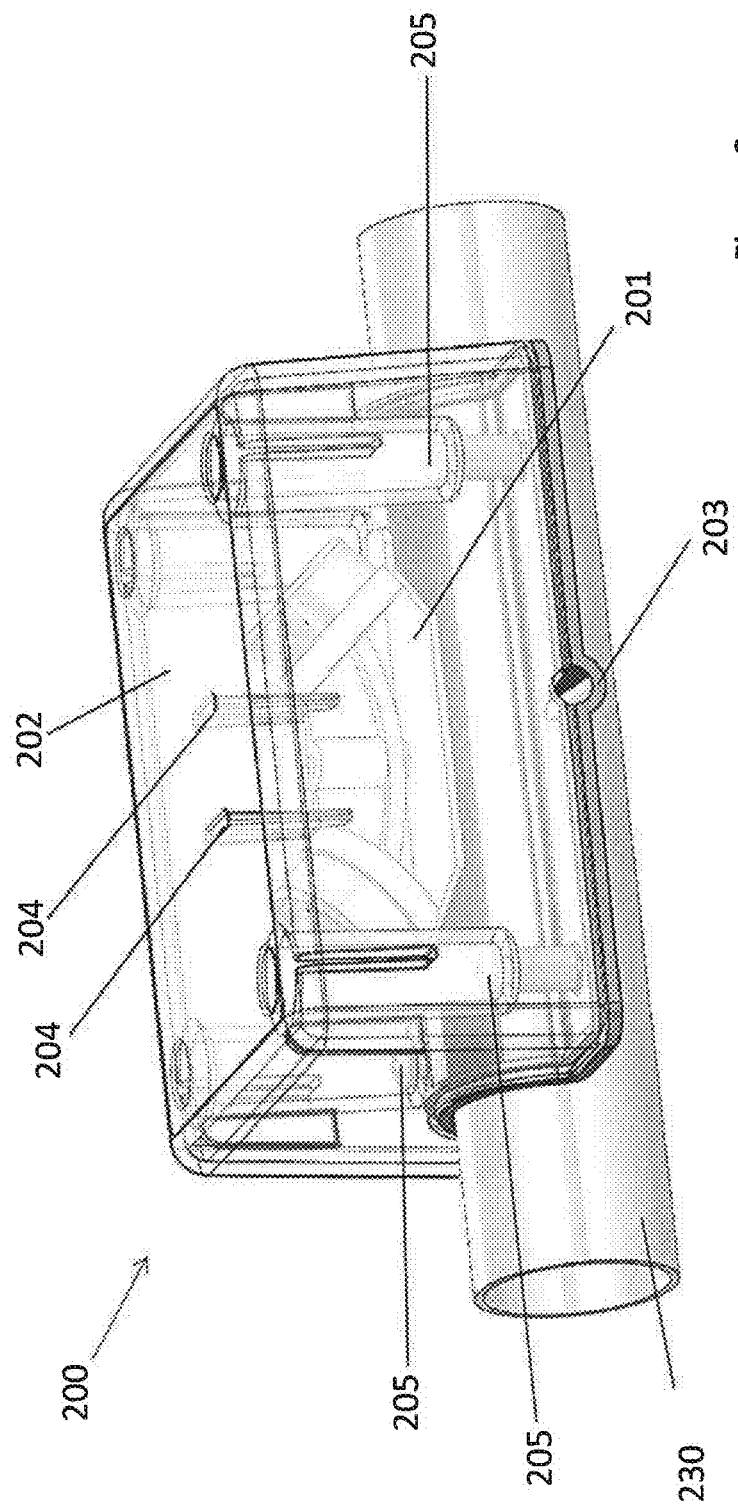
FIG. 3 illustrates a sensor cradle disposed in a protective housing in accordance with example implementations.

FIG. 3 illustrates a sensor cradle disposed in a protective housing in accordance with example implementations. FIG. 3 shows a translucent view of a sensor assembly 200 engaging pipe 230 in accordance with exemplary embodiments. The sensor assembly 200 includes an outer shell portion 202, an inner mounting portion 203, and a sensor cradle 201 coupled together in accordance example implementations. As illustrated in FIG. 3, the outer shell portion 202 can engage the sensor cradle 201 via alignment post 204. The alignment post 204 can maintain the sensor cradle perpendicular to the pipe wall and parallel to the pipe longitudinal axis without rigidly constraining motion in these directions. This reduces sensitivity of the sensor cradle to mechanical distortion that may be caused during thermal expansion and contraction over a range of operating temperatures due to differences in the coefficients of thermal expansion of the sensor cradle, the outer shell, the inner mount, and the pipe. The outer shell portion 202 can also be coupled to the inner mounting portion 203 via a plurality of fasteners 205, which may include fasteners such as screws. As will be demonstrated further herein, fasteners 205 may be removed from the assembly to access the sensor cradle 201. In some implementations, the outer shell portion 202 can be coupled to the inner mounting portion 203 via snapping mechanical elements capable of snapping to each other or via other coupling mechanisms known in the art. Various components of the sensor assembly illustrated in FIG. 3 may be manufactured by a process such as injection molding, which process may be used to produce various components such as the outer shell portion 202, the inner mounting portion 203, or the sensor cradle 201 out of materials such as plastic or other polymers including acrylic, polycarbonate, polysulfone, polystyrene, nylon, and polypropylene.

Figure 4:
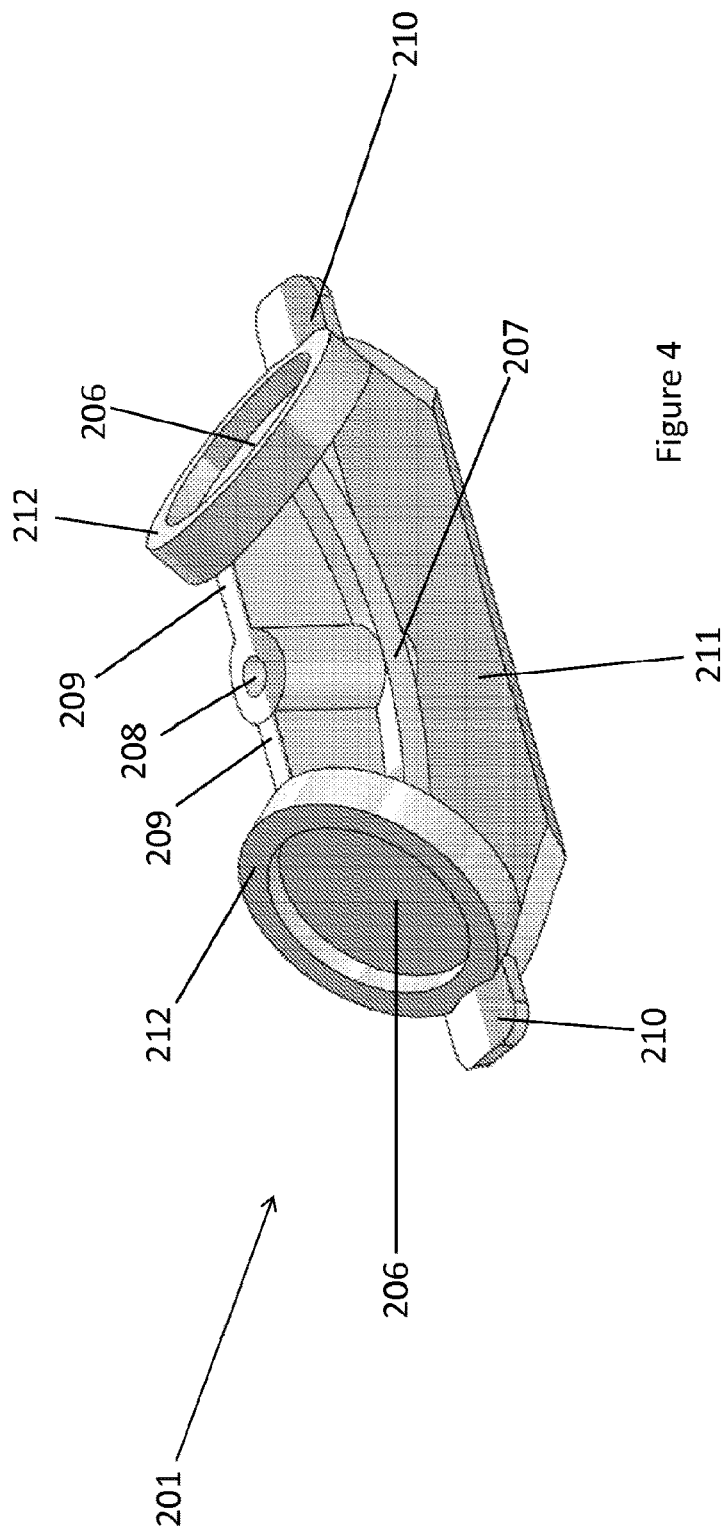
FIG. 4 illustrates the sensor cradle of FIG. 3 without the protective housing.

FIG. 4 illustrates the sensor cradle of FIG. 3 without the protective housing. The sensor cradle 201 is configured to seat transducers, such as ultrasonic transducers, such that the transducers engage recessed mounting surface 206 having a mounting flange 212 disposed about a peripheral portion of the recessed mounting surface 206. The sensor cradle 201 may include a signal wave-guide 207 for guiding a signal such as an ultrasonic wave transmitted by a sensor positioned in the sensor cradle 201 from one transducer in the cradle to a second transducer in the sensor cradle 201. In example embodiments, the transmission of a signal from one transducer in the sensor cradle 201 to the other transducer in the sensor cradle 201 via the waveguide 207 provides a reference signal that is used to calculate a temperature compensation factor that can be implemented to correct the signal output for variations in temperature of fluid in the pipe. The sensor cradle 201 can also include an integral bore 208 configured and positioned for housing an auxiliary component such as a thermistor or another sensor in accordance with example implementations. Bore 208 may be positioned close to the path of projected propagation of the signal or waves from transducers disposed in the recessed mounting surface 206 without actually being in the projected propagation path, which position may be substantially central in the block to increase thermal distribution in the body of the sensor cradle 201. As demonstrated in the illustrated embodiment, bore 208 may be positioned along a stabilizer track 209 configured for aligning and positioning the sensor cradle 201 within the outer shell portion 202 by engaging alignment posts 204. The sensor cradle 201 may also include one or more ledges 210 configured to engage the inner mounting portion 203 as demonstrated further herein. The sensor cradle 201 includes a curved pipe interface 211. In some implementations, sensor cradle 201 can include a flat pipe interface instead of a curved pipe interface.

Figure 5:
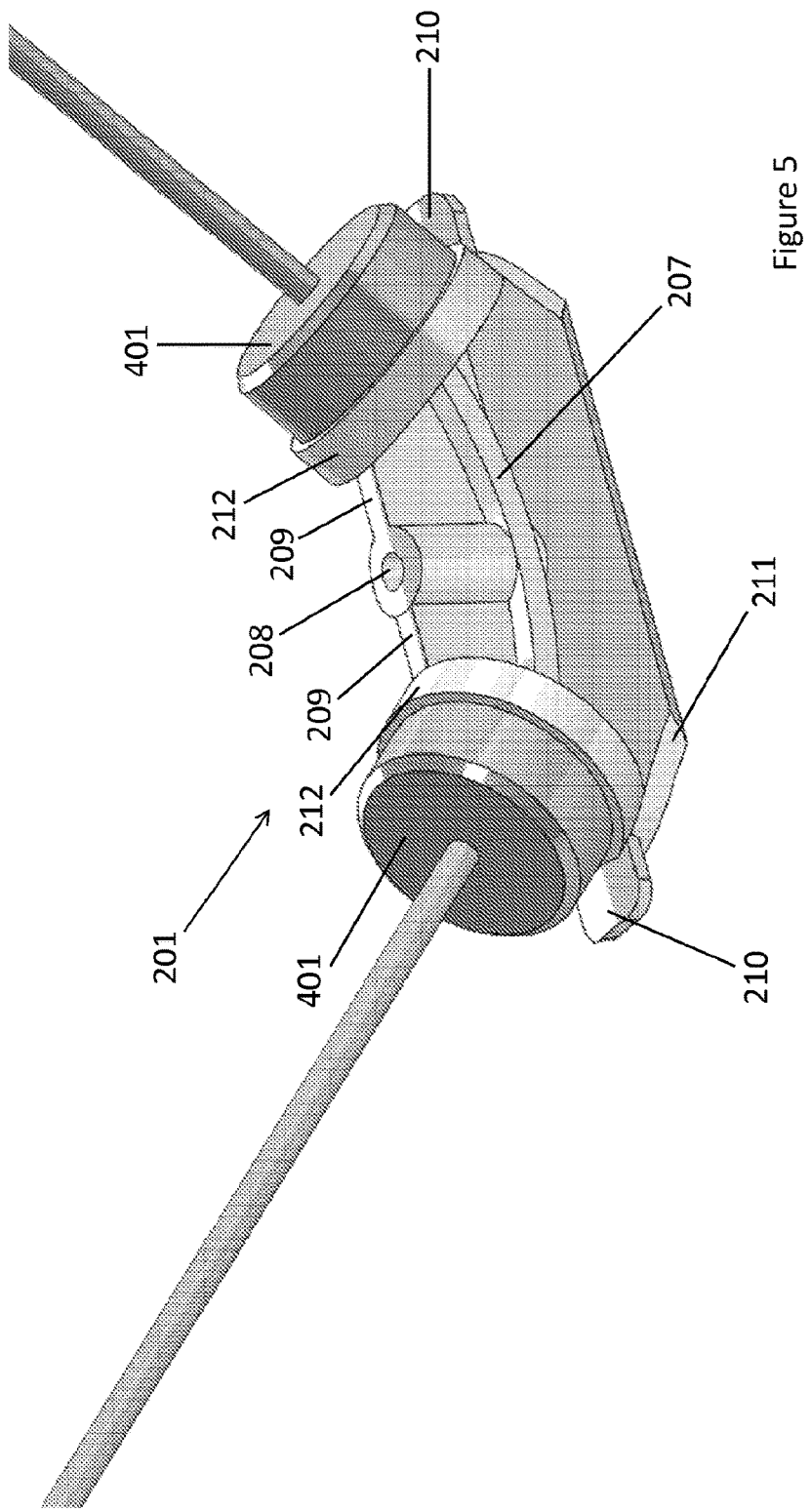
FIG. 5 illustrates the sensor cradle of FIG. 4 having transducers for measuring characteristics of fluid (e.g. flow) positioned therein in accordance with example implementations.

FIG. 5 illustrates the sensor cradle of FIG. 4 having transducers for measuring characteristics of fluid flow positioned therein in accordance with example implementations. Transducers 401 are positioned within mounting flange 212 of the sensor cradle 201 such that the transducers engage the recessed mounting surface 206. In accordance with example implementations, transducers 401 may be coupled to the recessed mounting surfaces 206, for example via a bond such as an adhesive bond. The recessed mounting surfaces 206 are configured with respect to one another on the sensor cradle 201 at the desired angular alignment and distance thereby providing passive alignment for the transducer's disposed therein. The alignment provided by the recessed mounting surfaces 206 causes the signal transmitted by transducers 401, which may be ultrasonic transducers in accordance with example implementations, to propagate into a pipe engaged with the curved pipe interface 211 and to traverse one another. Transducers can be fixed to the sensor cradle using epoxy or other suitable adhesive that allows signal propagation from the transducers into the sensor cradle, or can be temporarily positioned using a wet or dry couplants such as index matching fluids, greases, or gels.

Figure 6:
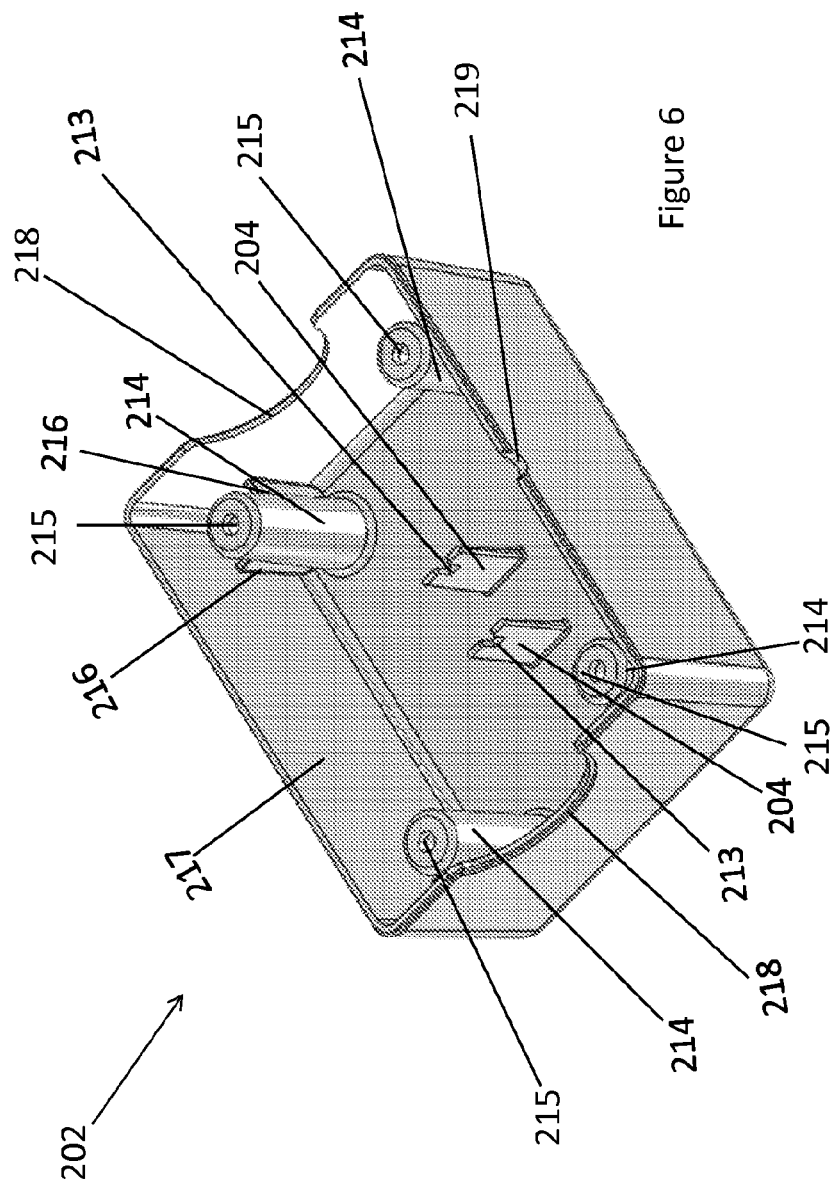
FIG. 6 is bottom perspective view of the outer shell portion of the protective housing of FIG. 3.

FIG. 6 is bottom perspective view of the outer shell portion of the protective housing of FIG. 3. The outer shell portion 202 includes one or more alignment posts 204 having a groove 213 disposed therein for engaging stabilizer track 209 on the sensor cradle 201. While the outer shell portion 202 shown in FIG. 6 includes two alignment posts 204, a single alignment post 204 or more than two alignment posts 204 can be employed in accordance with example implementations. The position of the sensor cradle 201 can be adjusted longitudinally through posts 204 along an axis running through grooves 213. The outer shell portion 202 may be composed of a material distinct from the sensor cradle 201 in accordance with example implementations. The outer shell portion 202 can include a plurality of cylindrical posts 214 for receiving fasteners 205 therein and extendable through apertures 215 to engage the outer shell portion 202 with the inner mounting portion 203. For example, the heads of fasteners 205 can remain within cylindrical posts 214 while the fastener bodies can extend through apertures 215 and into mating sections on the inner mounting portion 203. In some implementations, fasteners 205 can be integral with cylindrical posts 214. In the protective housing illustrated in FIG. 6, the cylindrical posts 214 can include struts 216 for stabilizing the cylindrical posts 214 with respect to walls 217 of the outer shell portion 202. The outer shell portion 202 can also include curved recesses 218 corresponding to a curved wall of the inner mounting portion 203 configured for engagement with pipe 230. The outer shell portion 202 can also include curved recess 219 for cable access for power and or signal cables. The position and morphology of recess 219 may be adapted to suit particular applications.

Figure 7:
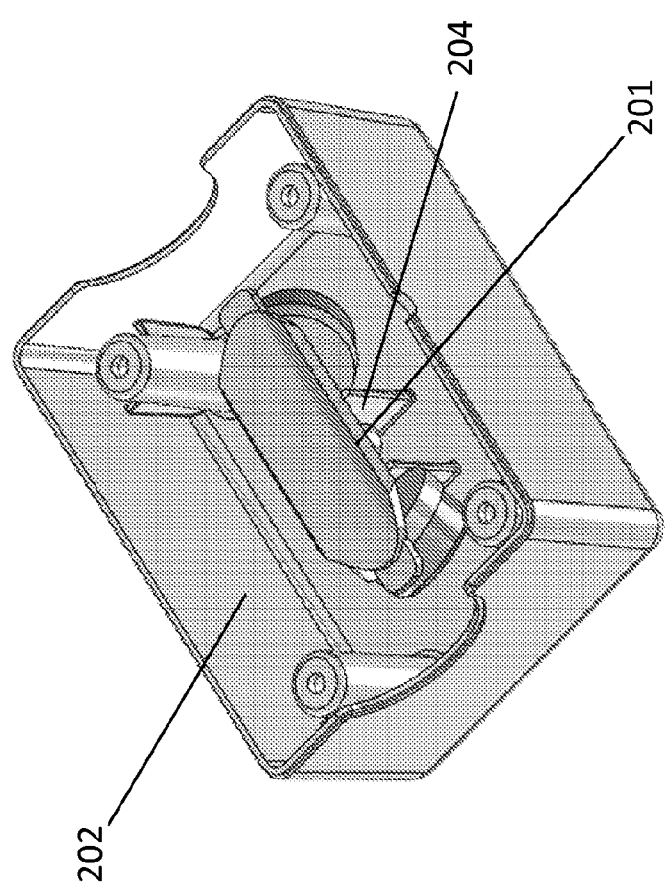
FIG. 7 is a bottom perspective view of the sensor cradle disposed in an opened protective housing of FIG. 3.

FIG. 7 is a bottom perspective view of the sensor cradle 201 disposed in the outer shell portion 202, in accordance with example implementations. As discussed herein, the sensor cradle 201 is positioned within outer shell portion 202 via engagement of the stabilizer track 209 of the sensor cradle 201 with the grooves 213 in the alignment post 204. The outer shell portion 202 in combination with the inner mounting portion 203 provide thermal and mechanical protection for the transducers disposed in the sensor cradle 201. Furthermore, the engagement of stabilizer track 209 and alignment post 204 permit the sensor cradle 201 to float along the stabilizer track 209 to help prevent thermal or mechanical loading of the sensor cradle 201.

Figure 8:
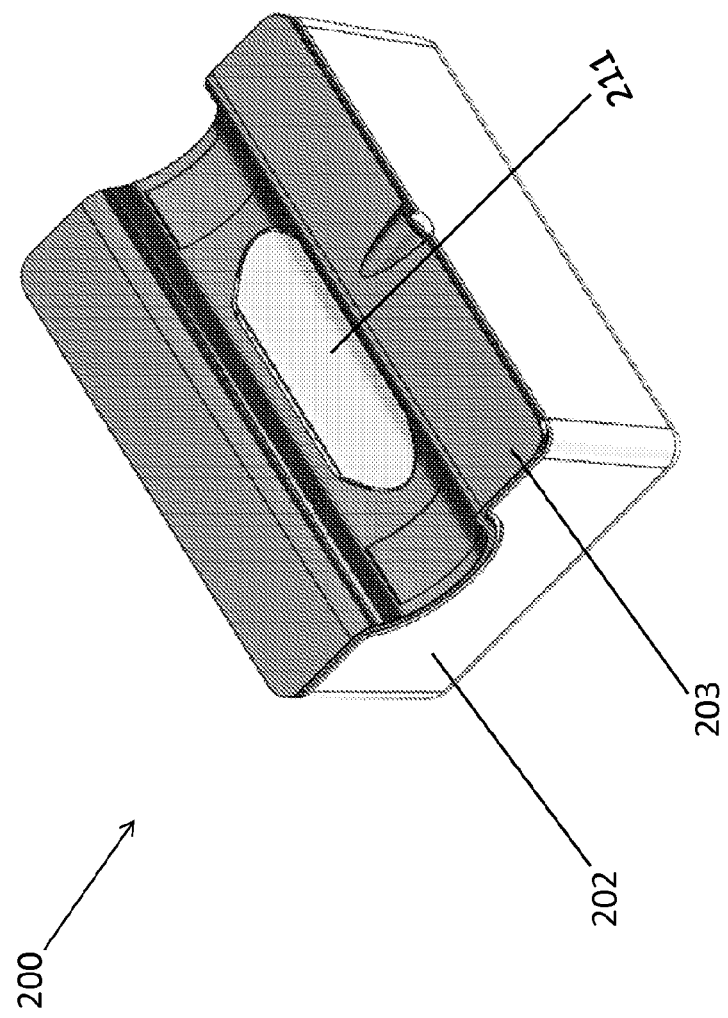
FIG. 8 is a bottom perspective view of the sensor cradle disposed in the closed protective housing of FIG. 3.

FIG. 8 is a bottom perspective view of the sensor cradle disposed in the closed protective housing of FIG. 3. FIG. 8 shows the sensor cradle 201, the outer shell portion 202 and the inner mounting portion 203 coupled together. As demonstrated in FIG. 8, the curved pipe interface 211 extends through a surface of the inner mounting portion 203 for engagement with a pipe, such as pipe 230. In accordance with example implementations, the inner mounting portion 203 may be composed of a material distinct from the outer shell portion 202 and the sensor cradle 201.

Figure 9:
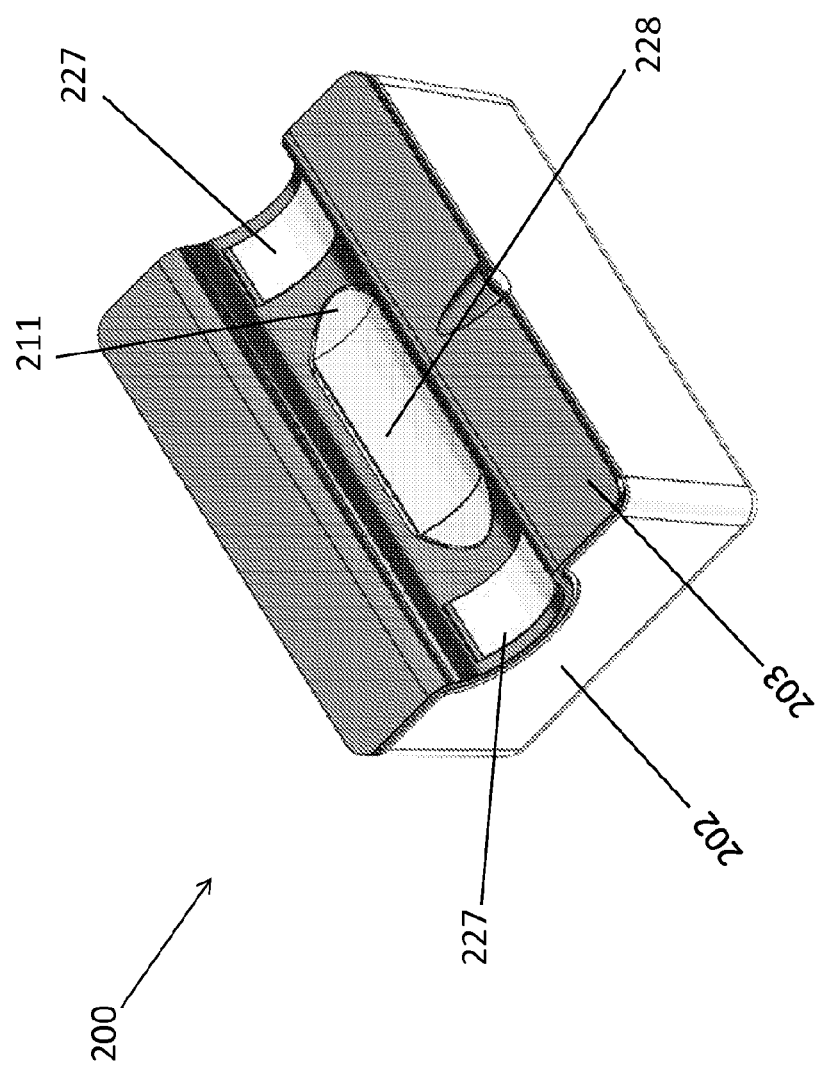
FIG. 9 shows a bottom perspective view of the sensor cradle disposed in the closed protective housing of FIG. 3 ready for mounting.

FIG. 9 shows a bottom perspective view of the sensor cradle disposed in the closed protective housing of FIG. 3 ready for mounting. As demonstrated in FIG. 9, sensor assembly 200 may be equipped with optional mounting pads 227, 228 disposed on the curved pipe interface 211 of the sensor cradle 201 and on pipe interface 220 of the inner mounting portion 203. The optional mounting pads 227, 228 may include an adhesive compound for matingly engaging the sensor assembly with pipe 230. The adhesive compound may include a pressure sensitive adhesive tape. In some implementations, the sensor cradle may be coupled to a pipe with a coupling agent such as a gel disposed between the pipe and the pipe interface.

Figure 10:
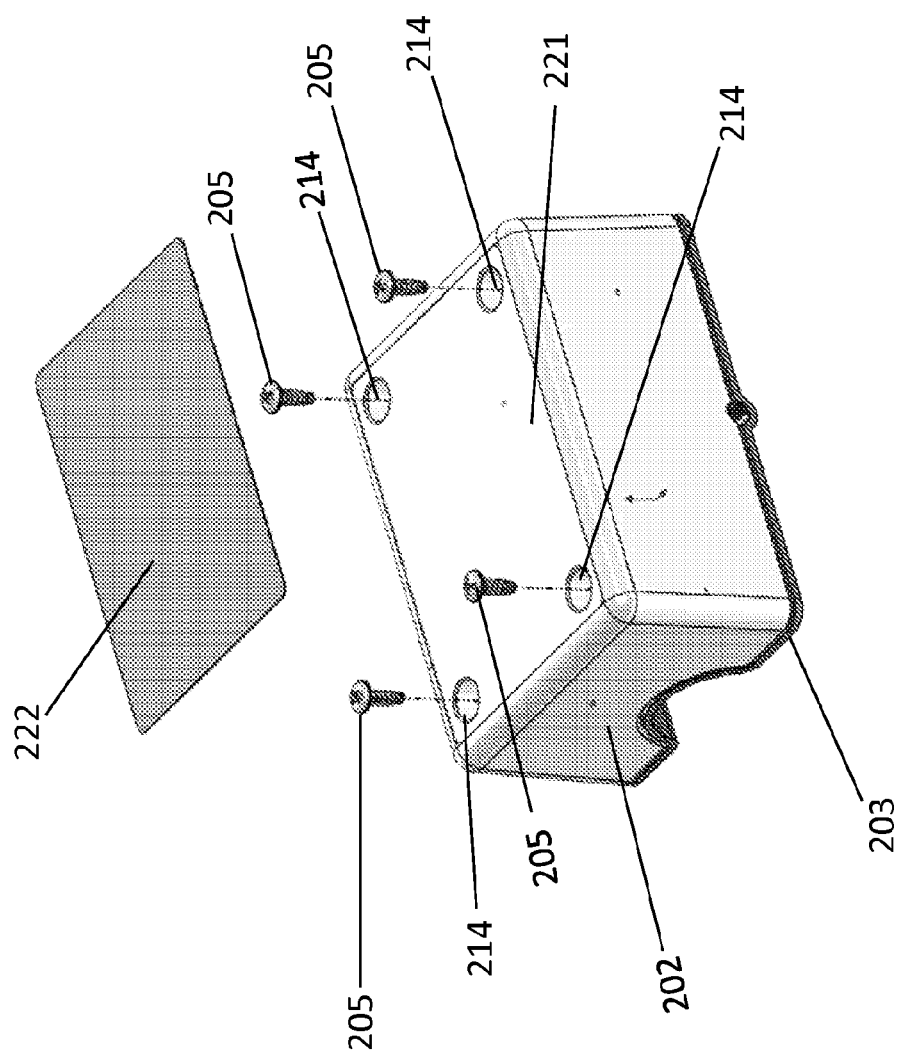
FIG. 10 provides a partially exploded view of the closed protective housing of FIG. 3.
Figure 11:
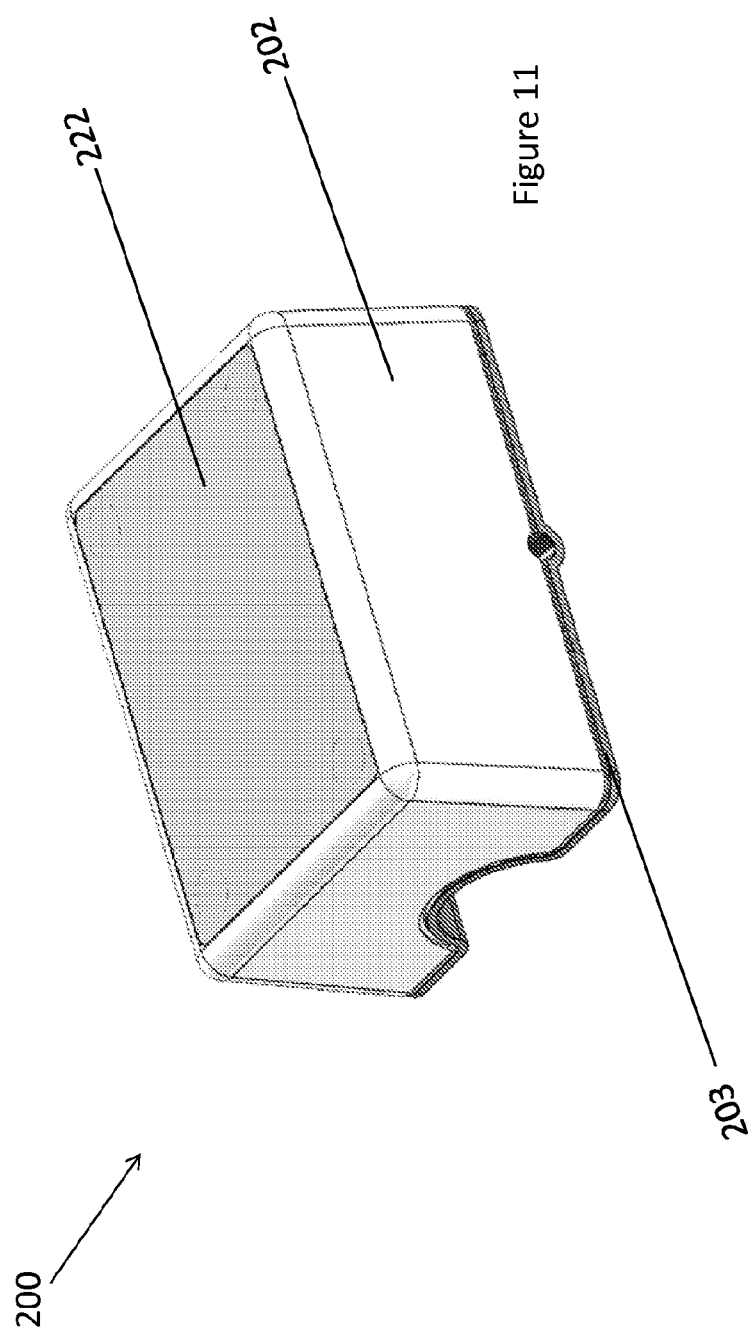
FIG. 11 provides an assembled outer view of FIG. 10.

FIG. 10 provides a partially exploded view of the closed protective housing of FIG. 3. As demonstrated in FIG. 10, the outer shell portion 202 may be coupled to the inner mounting portion via a plurality of fasteners 205 inserted into cylindrical posts 214. The outer shell portion 202 may include a recessed surface 221 configured to receive a cover plate 222 for concealing cylindrical posts 214 and fasteners 205 disposed therein. The cover plate may be comprised of an adhesive label, plastic sheet, or other suitable material. FIG. 11 provides an assembled outer view of FIG. 10 demonstrating the cover plate 222 positioned in recessed surface 221 of outer shell portion 202.

Figure 12:
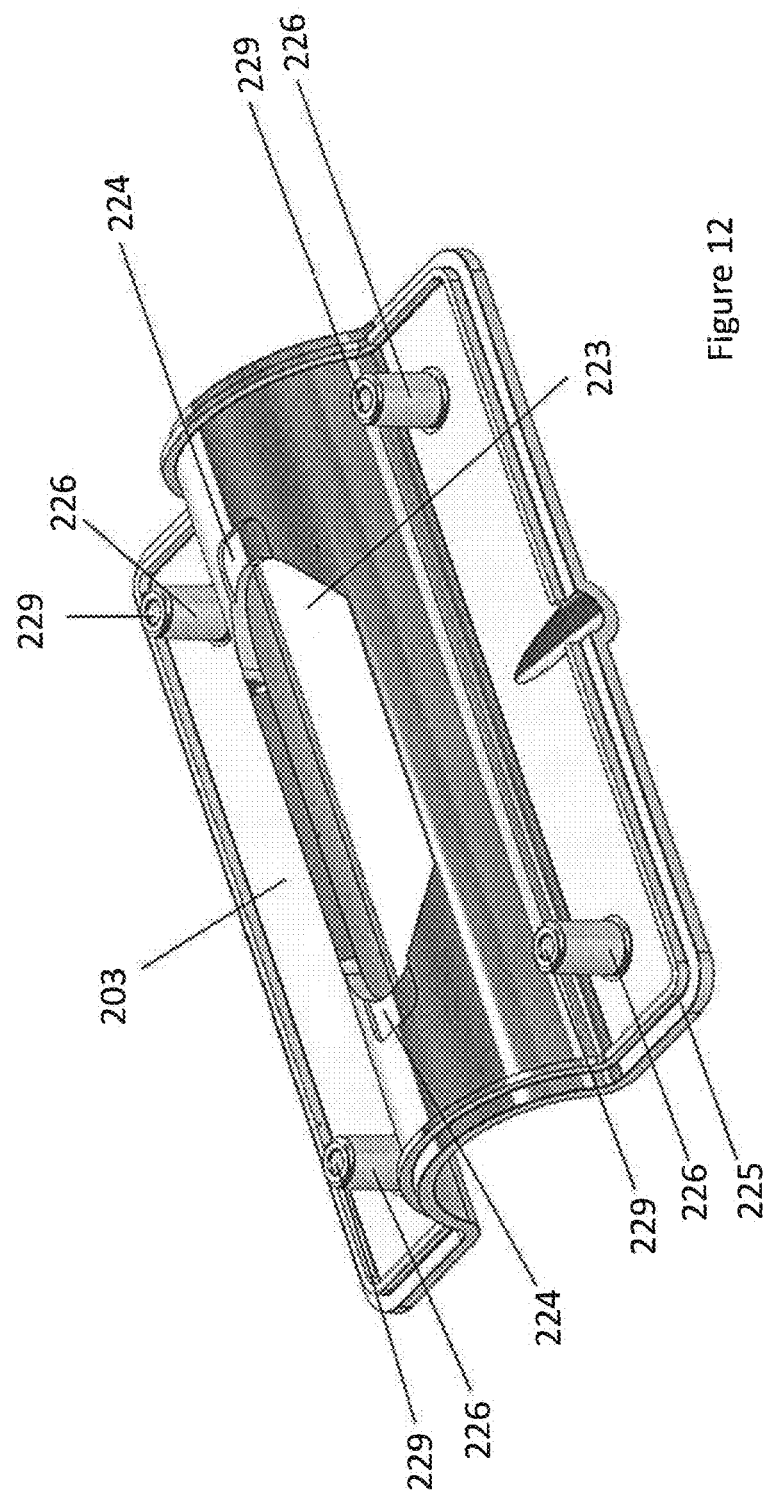
FIG. 12 shows the inside of the inner mounting portion of the protective housing of FIG. 3.

FIG. 12 shows the inside of the inner mounting portion of the protective housing of FIG. 3. As illustrated in FIG. 12, the inner mounting portion 203 includes an opening 223 for receiving the sensor 201. More specifically, opening 223 has a shape substantially corresponding to the shape of the curved pipe interface 211 of the sensor cradle 201. The inner mounting portion 203 also includes recesses 224 for engaging the ledges 210 of the sensor 201. The inner mounting portion 203 may also include a ridge 225. Ridge 225 may assist with aligning the inner mounting portion 203 with respect to the outer shell portion 202. Ridge 225 may be composed of the same material as the remainder of inner mounting portion 203. In some implementations, ridge 225 can be composed of a distinct material, such as a rubber material and may serve as a gasket between the inner mounting portion 203 and the outer shell portion 202. The inner mounting portion 203 includes a plurality of engagement footing 226 corresponding in location to the locations of cylindrical posts 214 and including openings 229 for receiving the body of fasteners 205. The engagement footings 226 may include a grooved inner surface configured to matingly engage with fasteners 205.

Figure 13:
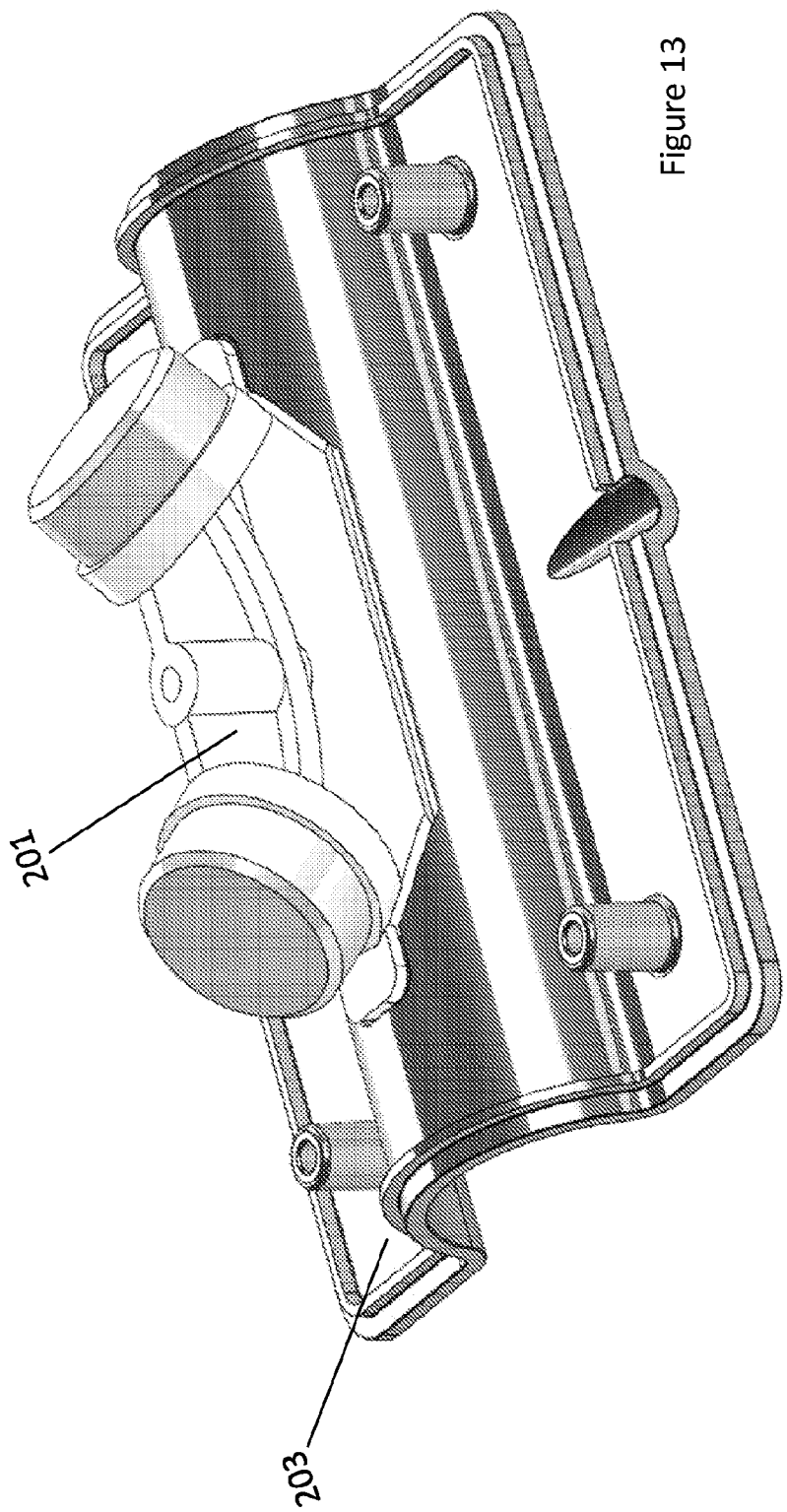
FIG. 13 shows the inside of the inner mounting portion of FIG. 12 with the sensor cradle having transducers coupled thereto in accordance with example implementations.

FIG. 13 shows the sensor 201 engaged with the inner mounting portion 201 such that curved pipe interface 211 extends through opening 223 and ledges 210 engage recesses 224 in accordance with example implementations.

Figure 14A:
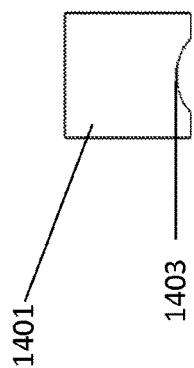
FIGS. 14A-14E illustrate a sensor cradle including a wave-guide in accordance with example implementations.
Figure 14B:
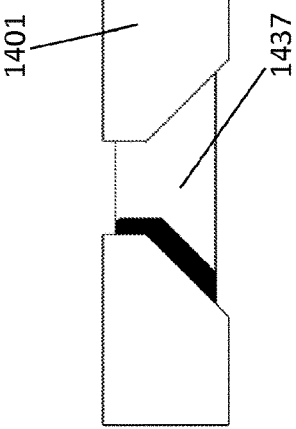
Figure 14C:
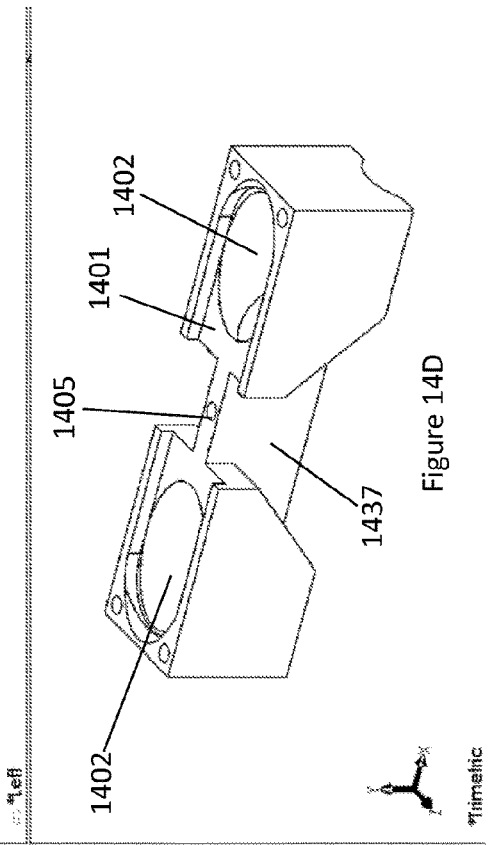
Figure 14D:
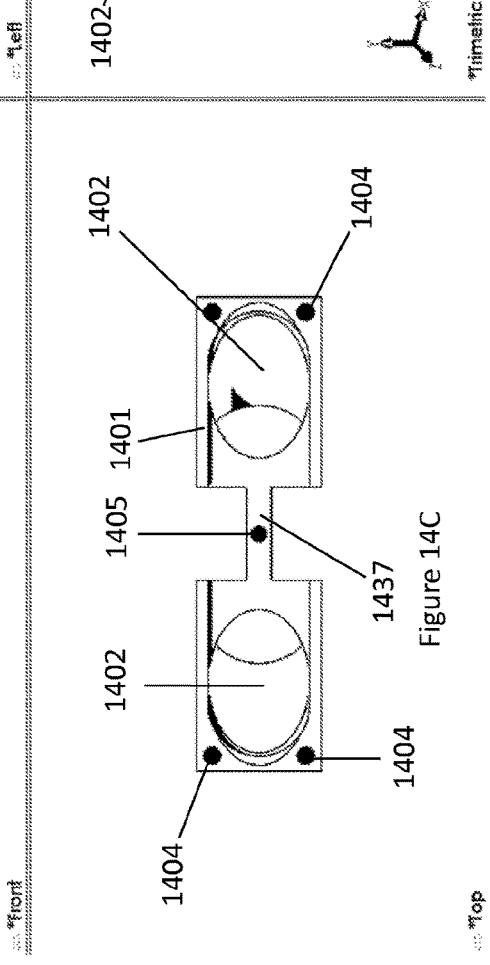
Figure 14E:
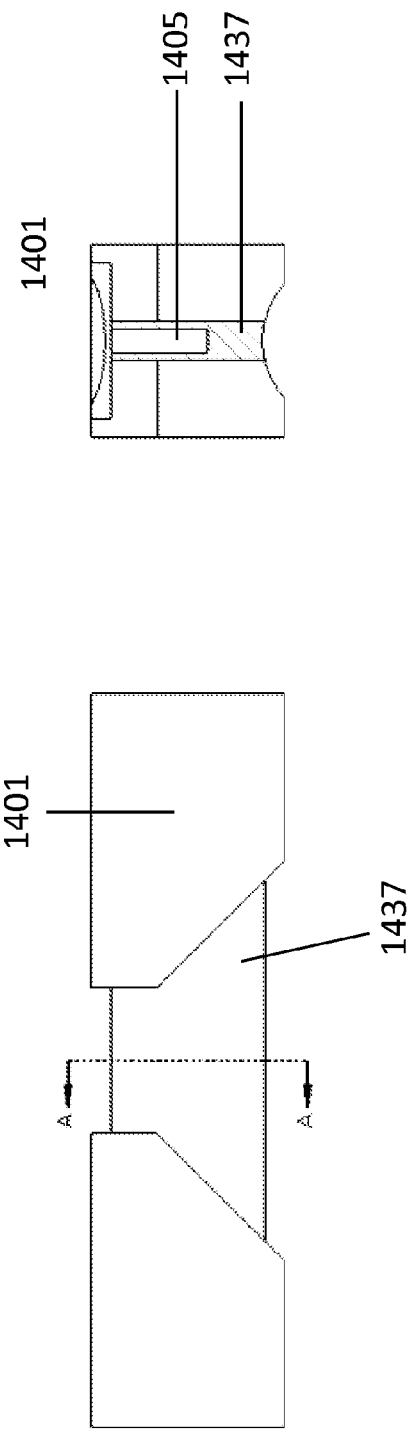

FIGS. 14A-14E illustrate a sensor cradle including a wave-guide in accordance with example implementations. FIG. 14A provides a side view of sensor cradle 1401. FIG. 14B provides an end view of the sensor cradle 1401. FIG. 14C provides a top view of the sensor cradle 1401. FIG. 14D provides a perspective view of the sensor cradle 1401. FIG. 14E provides a cross sectional view of the sensor cradle 1401. The sensor cradle 1401 includes a wave-guide 1437 positioned between two transducer openings 1402. The wave-guide 1437 transmits sound energy (from a transducer) radially into a pipe coupled to the sensor cradle at curved interface 1403, thereby permitting the pipe to transmit back in a corresponding parallel direction. The transmission path created by wave-guide 1437 helps eliminate broader sound propagation and echoing, thereby reducing the noise in signals reflected back into transducers disposed in transducer openings 1402. The wave-guide 1437 may be composed of the same material as the cradle 1401 or it may be composed of a distinct material. For example, the wave-guide 1437 may be composed of a metallic material such as aluminum, while the sensor cradle 1401 may be composed of a plastic material. In some implementations, the wave-guide 1437 may include a central notch disposed therein to assist in disrupting the propagation of unwanted waves such as shear and/or longitudinal waves into the pipe coupled to the sensor cradle 1401.

The transducer openings 1402 are configured for seating and maintaining transducers, such as ultrasonic transducers, for measuring properties of fluid flowing in the wave path of the transducers. The transducer openings 1402 are configured to orient the transducers for wave transmission traversing a pipe positioned adjacent to the cradle. In the sensor cradle illustrated in FIGS. 14A-14E, the transducer openings 1402 are configured to orient transducers or flow meters positioned therein such that the transducers will transmit waves substantially orthogonal with respect to one another. The curved interface 1403 is configured for engaging the sensor cradle 1401 with a conduit, such as a pipe for transferring fluids, including but not limited to water and gas. In accordance with example implementations, transducers disposed in the transducer openings 1402 may be configured to measure fluid properties including, but not limited to, fluid flow rate and fluid temperatures. In accordance with example implementations, transducers disposed in the transducer openings 1402 can be configured to compensate for the temperature of the fluid and of the sensor cradle. In some implementations, the angle of orientation of the transducer openings 1402 may be configured in accordance with properties of a particular pipe, such as pipe material and pipe geometry. The sensor cradle 1401 may also include a plurality of fastener openings 1404, which may be used to fasten an outer shroud or covering to the sensor cradle 1401. The sensor cradle 1401 may also include one or more bore holes configured and positioned for housing an auxiliary component such as a thermistor in accordance with example implementations. In accordance with example implementations, sensor cradle 1401 may be configured with transducers positioned the sensor cradle 1401 at or between 0°-85° with respect to an axis perpendicular to the curved interface 1403 and/or the pipe wall coupled to the sensor cradle. In accordance with example implementations, sensor cradle 1401 may be composed of a combination of one or more metals (including but not limited to aluminum or copper) and polymers (including but not limited to plastics such as acrylic, polycarbonate, polysulfone, polystyrene, nylon, and polypropylene.

Figure 15B:
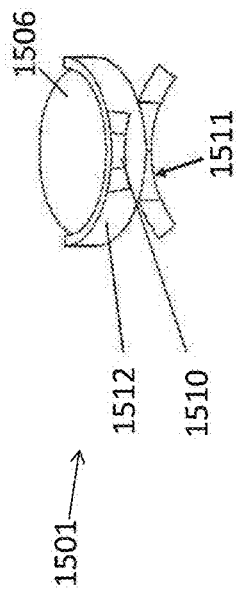
FIGS. 15A-15D illustrate a sensor cradle including dual wave-guides and configured for disposition within a housing guide in accordance with example implementations.
Figure 15A:
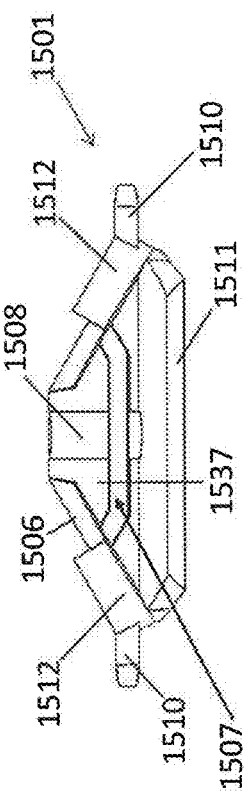
Figure 15D:
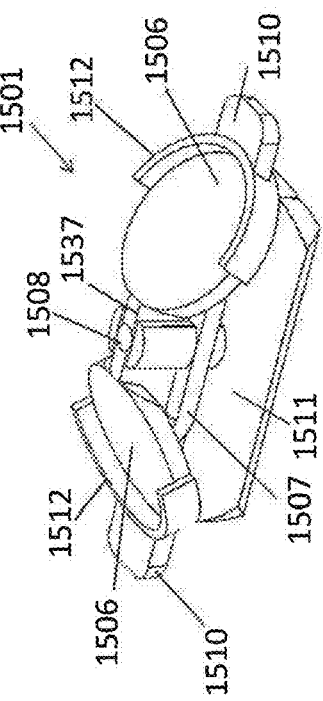
Figure 15C:
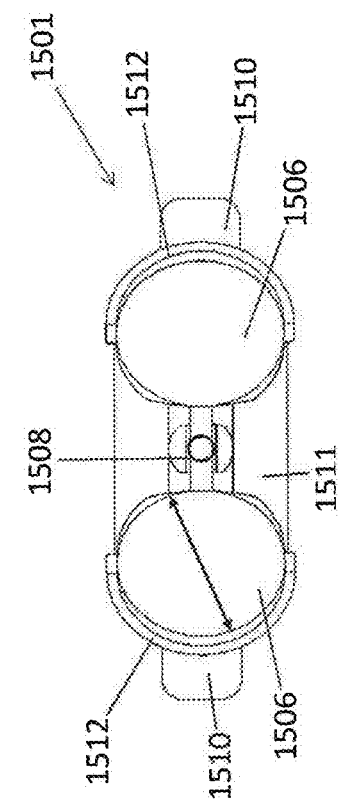

FIGS. 15A-15D illustrate a sensor cradle including dual wave-guides and configured for disposition within a housing guide in accordance with example implementations. FIG. 15A provides a side view of sensor cradle 1501. FIG. 15B provides an end view of the sensor cradle 1501. FIG. 15C provides a top view of the sensor cradle 1501. FIG. 15D provides a perspective view of the sensor cradle 1501. The sensor cradle 1501 is configured to seat transducers, such as ultrasonic transducers, such that the transducers engage mounting surface 1506 having a semi-circular mounting flange 1512 disposed about a peripheral portion of the recessed mounting surface 1506. The semi-circular mounting flanges 1512 facilitate injection molding of sensor cradle 1501. The sensor cradle 1501 may include a signal wave-guide 1507 for guiding a signal, such as an ultrasonic waves, between sensors positioned in the sensor cradle 1501. Rib 1537 provides a second wave-guide for directing transmission from sensors positioned in the sensor cradle 1501 into the pipe and for receiving transmission reflected back out of the pipe. Rib 1537 causes substantially vertical transmission in to the pipe. Rib 1537 may be composed of a distinct material from other portions of the sensor cradle 1501, such as aluminum, or other materials having a higher sound velocity than the material of the sensor cradle 1501. The sensor cradle 1501 may also include an integral bore 1508 configured and positioned for housing an auxiliary component such as a thermistor in accordance with example implementations. Bore 1508 may be positioned close to the path of projection of the signal or waves from transducers disposed in the recessed mounting surface 1506 without actually being in the projected propagation path, which position may be substantially central in the block to increase thermal distribution in the body of the sensor cradle 1501. The sensor cradle 1501 may also include one or more tabs 1510 configured to engage a housing for the sensor cradle and retain the sensor cradle 1501 in a position for assembly and installation while still permitting the sensor cradle 1501 to float. The ability of the sensor cradle 1501 to float reduces stress on the transducers caused by coupling and/or temperature variations. The tabs 1510 can extend from a curved pipe interface 1511 of the sensor cradle 1501.

In accordance with example implementations, sensor cradle 1501 may be configured with transducers positioned the sensor cradle 1501 at or between 0°-85° with respect to an axis perpendicular to the curved interface 1511 and/or the pipe wall coupled to the sensor cradle. In accordance with example implementations, sensor cradle 1501 may be composed of a combination of one or more metals (including but not limited to aluminum or copper) and polymers (including but not limited to plastics such as acrylic, polycarbonate, polysulfone, polystyrene, nylon, and polypropylene.

Figure 16B:
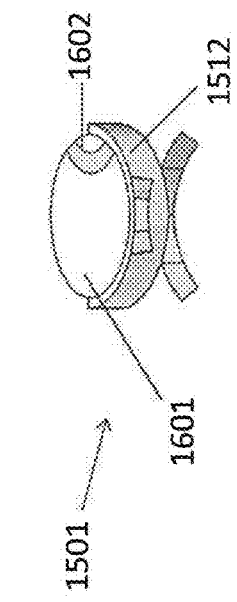
FIGS. 16A-16D illustrate the sensor cradle of Figures FIGS. 15A-15E having transducers coupled thereto in accordance with example implementations.
Figure 16A:
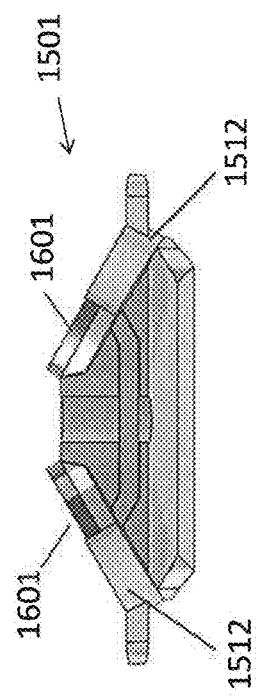
Figure 16D:
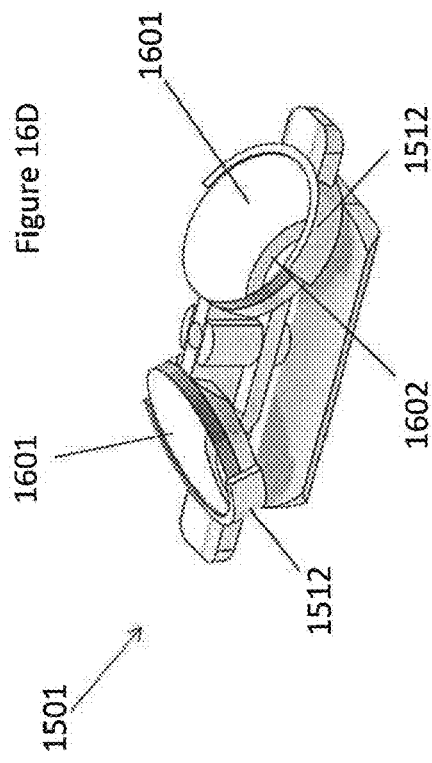
Figure 16C:
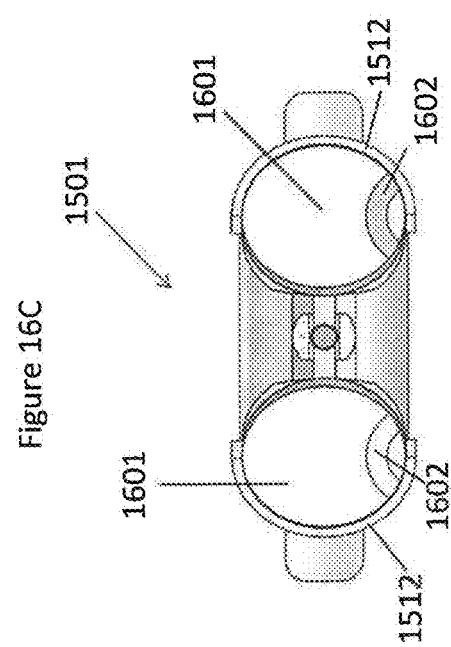

FIGS. 16A-16D illustrate the sensor cradle of Figures FIGS. 15A-15E having transducers coupled thereto in accordance with example implementations. Transducers 1601, which may include, but are not limited to, piezo-electric transducers are positioned on mounting surface 1506 of the sensor cradle 1501. The transducers 1601 are aligned on the mounting surfaces 1506 via mounting flanges 1512. As shown in FIG. 16C, transducers 1601 are aligned such that the contacts 1602 are disposed outside of the transmission path through the wave-guide 1537 and may be positioned on corresponding sides. Arced contacts 1602 permit single sided soldering on transducers 1601. While mounting surfaces 1506, flanges 1512, and transducers 1601 are illustrated as circular components, such components can have non-circular shapes.

FIGS. 17A-17D illustrate another sensor cradle including dual wave-guides and configured for disposition within a housing guide in accordance with example implementations. FIG. 17A provides a side view of sensor cradle 1701. FIG. 17B provides an end view of the sensor cradle 1701. FIG. 17C provides a top view of the sensor cradle 1701. FIG. 17D provides a perspective view of the sensor cradle 1701. The sensor cradle 1701 is similar to cradle 1701, but has less and reduced features. For example, sensor cradle 1701 includes a truncated curved pipe interface 1711, and reduced transducer mounting surfaces 1706 having a semi-circular mounting flange 1712 disposed about a peripheral portion of the recessed mounting surface 1706. The semi-circular mounting flanges 1712 facilitate injection molding of sensor cradle 1701. The sensor cradle 1701 may include a signal wave-guide 1707 for guiding a signal, such as an ultrasonic waves, between sensors positioned in the sensor cradle 1701. Rib 1737 provides a second wave-guide for directing transmission from sensors positioned in the sensor cradle 1701 into the pipe and for receiving transmission reflected back out of the pipe. Rib 1737 may be composed of a distinct material from other portions of the sensor cradle 1701, such as aluminum, or other materials having a higher sound velocity than the material of the sensor cradle 1701. The sensor cradle 1701 may also include an integral bore 1708 configured and positioned for housing an auxiliary component such as a thermistor in accordance with example implementations.

In accordance with example implementations, sensor cradle 1701 may be configured with transducers positioned the sensor cradle 1701 at or between 0°-85° with respect to an axis perpendicular to the curved interface 1711 and/or the pipe wall coupled to the sensor cradle. In accordance with example implementations, sensor cradle 1701 may be composed of a combination of one or more metals (including but not limited to aluminum or copper) and polymers (including but not limited to plastics such as acrylic, polycarbonate, polysulfone, polystyrene, nylon, and polypropylene.

Figure 18A:
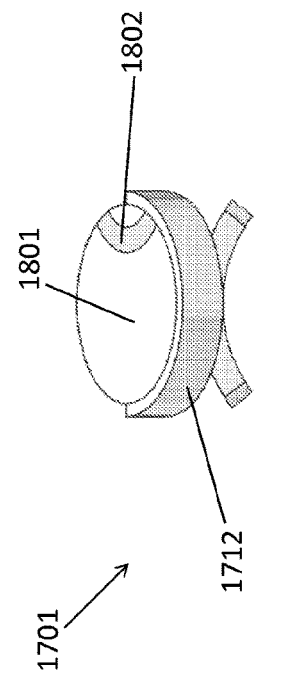
FIGS. 18A-18D illustrate the sensor cradle of FIGS. 17A-17D having transducers coupled thereto in accordance with example implementations.
Figure 18B:
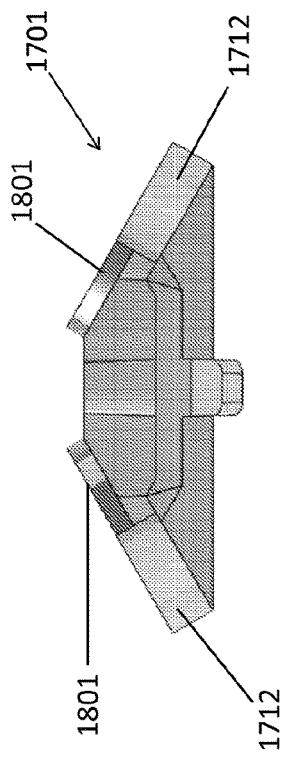
Figure 18C:
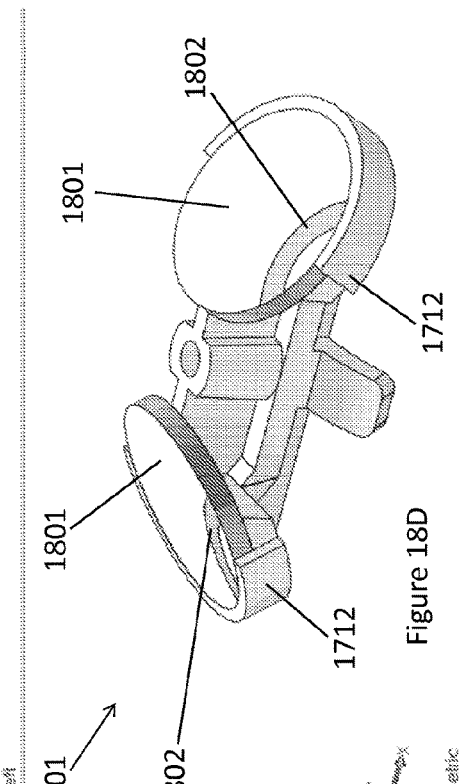
Figure 18D:
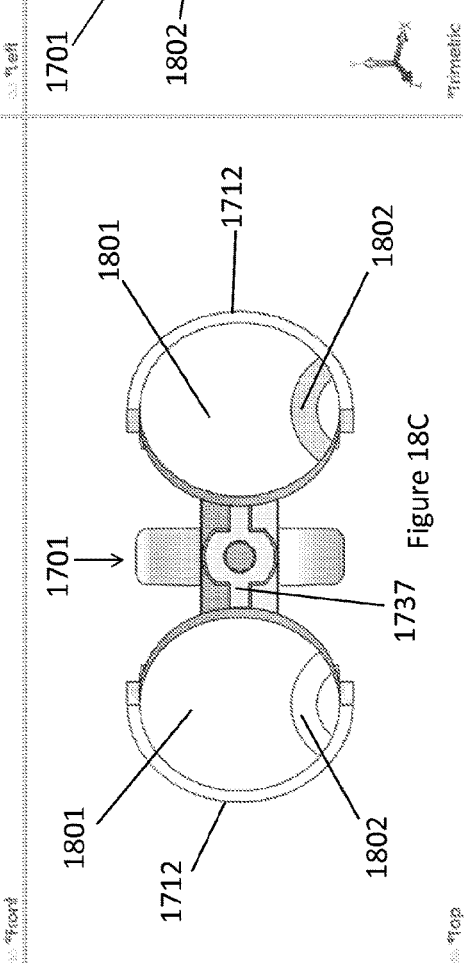

FIGS. 18A-18D illustrate the sensor cradle of FIGS. 17A-17D having transducers coupled thereto in accordance with example implementations. Transducers 1801, which may include, but are not limited to, piezo-electric transducers are positioned on mounting surface 1706 of the sensor cradle 1701. The transducers 1801 are aligned on the mounting surfaces 1706 via mounting flanges 1712. As shown in FIG. 18C, transducers 1801 are aligned such that the contacts 1802 are disposed outside of the transmission path through the wave-guide 1737 and may be positioned on corresponding sides. Arced contacts 1802 permit single sided soldering on transducers 1801.

FIGS. 19A-19D illustrate a trapezoidal sensor cradle in accordance with example implementations. FIG. 19A provides a side view of trapezoidal sensor cradle 1901. FIG. 19B provides an end view of the trapezoidal sensor cradle 1901. FIG. 19C provides a top view of the trapezoidal sensor cradle 1901. FIG. 19D provides a perspective view of the trapezoidal sensor cradle 1901. The trapezoidal sensor cradle 1901 provides a design that is easy to machine and allows for inventive embodiments to be provided at a reduced cost. The trapezoidal sensor cradle 1901 includes two sensor pads 1906. Pads 1906 may have a height and width corresponding to a diameter of a circular transducer in accordance with example implementations. The trapezoidal sensor cradle 1901 may an integral bore 1908 configured and positioned for housing an auxiliary component such as a thermistor in accordance with example implementations.

In accordance with example implementations, trapezoidal sensor cradle 1901 may be configured with transducers positioned the sensor cradle 1901 at or between 0°-85° with respect to an axis perpendicular to the pipe wall coupled to the sensor cradle. In accordance with example implementations, sensor cradle 1901 may be composed of a combination of one or more metals (including but not limited to aluminum or copper) and polymers (including but not limited to plastics such as acrylic, polycarbonate, polysulfone, polystyrene, nylon, and polypropylene.

FIGS. 20A-20D illustrate the trapezoidal sensor cradle of FIGS. 19A-19D having transducers coupled thereto in accordance with example implementations. Transducers 2001, which may include, but are not limited to, piezo-electric transducers are positioned on sensor pads 1906 of the sensor cradle 1901.

Figure 21A:
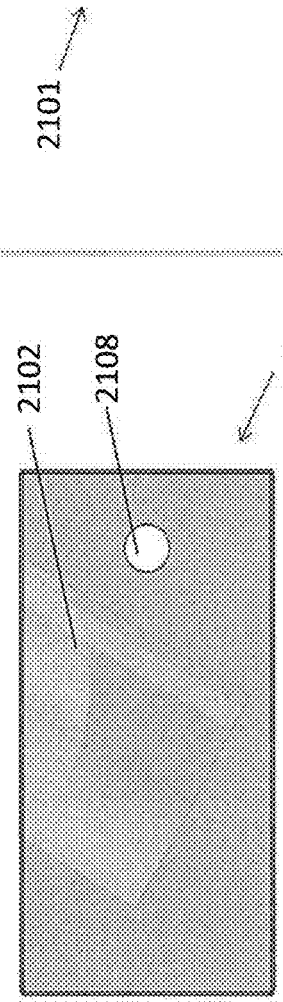
FIGS. 21A-21D illustrate a separable sensor cradle in accordance with example implementations.
Figure 21B:
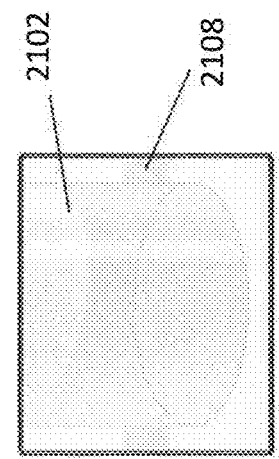
Figure 21C:
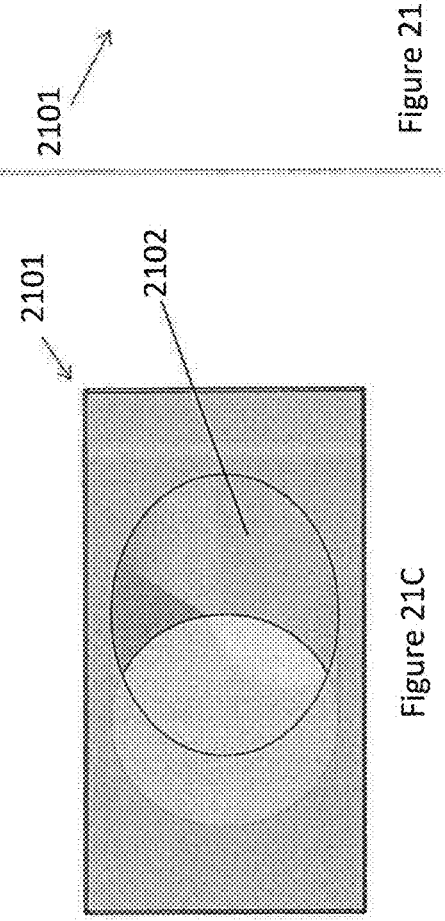
Figure 21D:
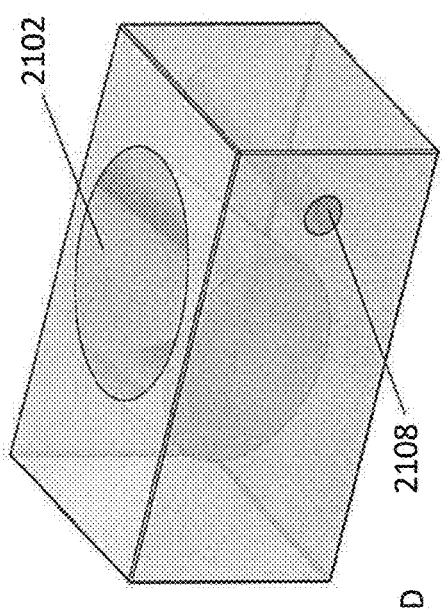

FIGS. 21A-21D illustrate a separable sensor cradle in accordance with example implementations. FIG. 21A provides a side view of separable sensor cradle 2101. FIG. 21B provides an end view of the separable sensor cradle 2101. FIG. 21C provides a top view of the separable sensor cradle 2101. FIG. 21D provides a perspective view of the separable sensor cradle 2101. Separable sensor cradle 2101 includes a sensor bore 2102 configured to retain a sensor at approximately 30 degrees with respect to a surface of the sensor cradle 2101 configured for contact with a pipe. The separable sensor cradle 2101 can include a thermistor bore 2108 in accordance with various example implementations.

FIGS. 22A-22D illustrate the separable sensor cradle of FIGS. 21A-21D having a transducer coupled thereto in accordance with example implementations. FIGS. 21A-21D show the separable sensor cradle 2101 with transducer 2201 disposed within the sensor bore 2102.

Figure 23B:
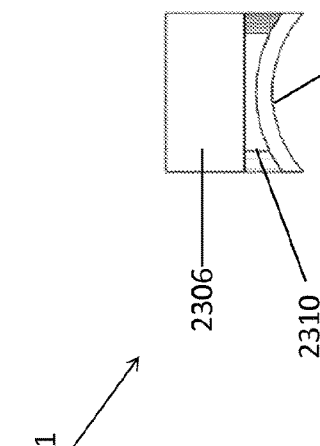
FIGS. 23A-23D illustrate another trapezoidal sensor cradle in accordance with example implementations.
Figure 23A:
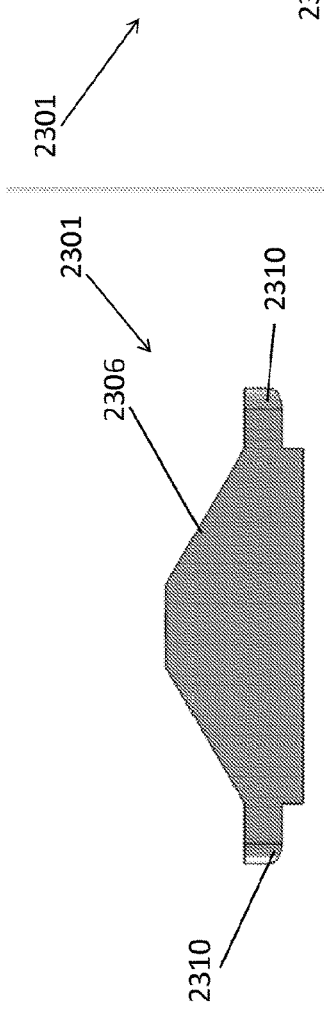
Figure 23D:
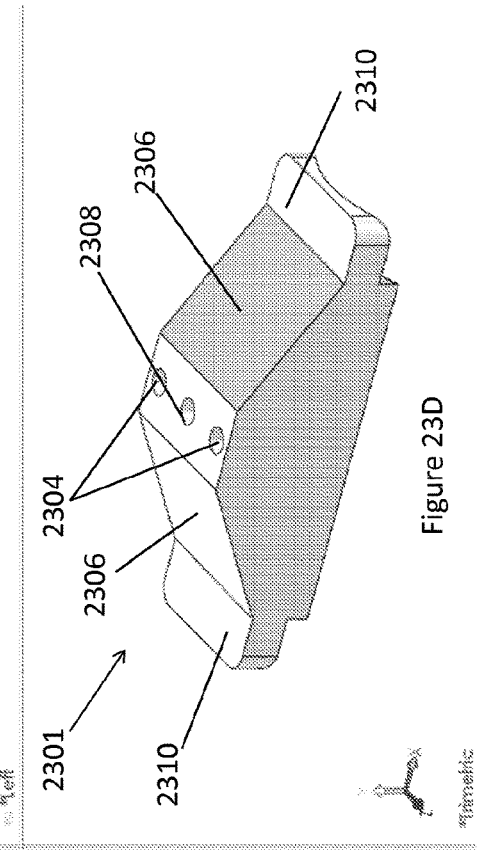
Figure 23C:
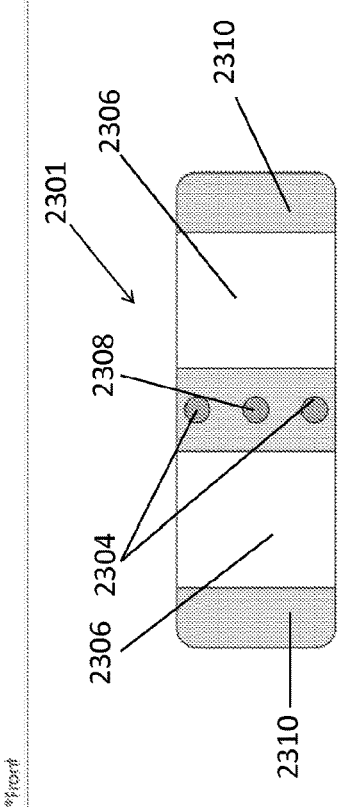

FIGS. 23A-23D illustrate another trapezoidal sensor cradle in accordance with example implementations. FIG. 23A provides a side view of trapezoidal sensor cradle 2301. FIG. 23B provides an end view of the trapezoidal sensor cradle 2301. FIG. 23C provides a top view of the trapezoidal sensor cradle 2301. FIG. 23D provides a perspective view of the trapezoidal sensor cradle 2301. The trapezoidal sensor cradle 2301 includes sensor pads 2306 for mounting transducers thereon. The trapezoidal sensor cradle 2301 includes tabs 2310 extending therefrom for engagement with a housing component. The trapezoidal sensor cradle 2301 may also include a thermistor bore 2308 and one or more alignment bores 2304 for alignment of the trapezoidal sensor cradle 2301 with a housing components such as a housing cover. The trapezoidal sensor cradle 2301 also includes a curved pipe interface 2311 configured to engage a pipe and align the trapezoidal sensor cradle 2301 therewith.

In accordance with example implementations, sensor cradle 2301 may be configured with transducers positioned the sensor cradle 2301 at or between 0°-85° with respect to an axis perpendicular to the curved interface 2311 and/or the pipe wall coupled to the sensor cradle. In accordance with example implementations, sensor cradle 2301 may be composed of a combination of one or more metals (including but not limited to aluminum or copper) and polymers (including but not limited to plastics such as acrylic, polycarbonate, polysulfone, polystyrene, nylon, and polypropylene.

FIGS. 24A-24D illustrate the trapezoidal sensor cradle of FIGS. 23A-23D having transducers coupled thereto in accordance with example implementations. Transducers 2401, which may include, but are not limited to, piezo-electric transducers are positioned on sensor pads 2306 of the sensor cradle 2301.

Figure 25B:
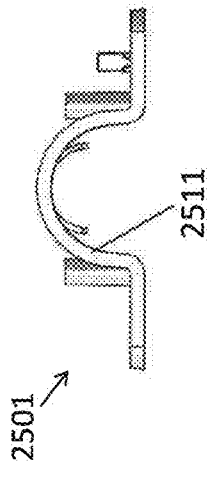
FIGS. 25A-25D show a mounting portion of a housing for a sensor cradle in accordance with example implementations.
Figure 25D:
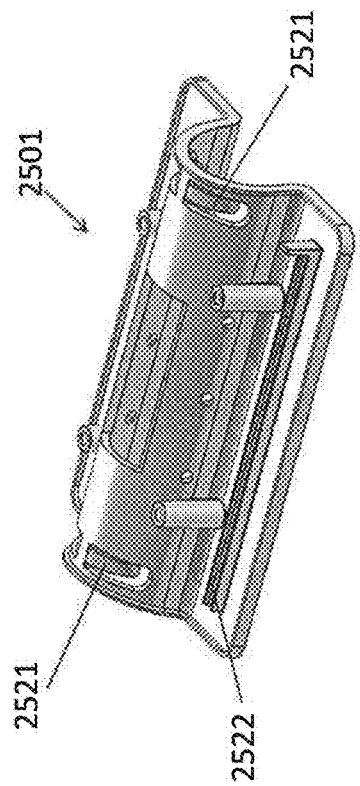
Figure 25A:
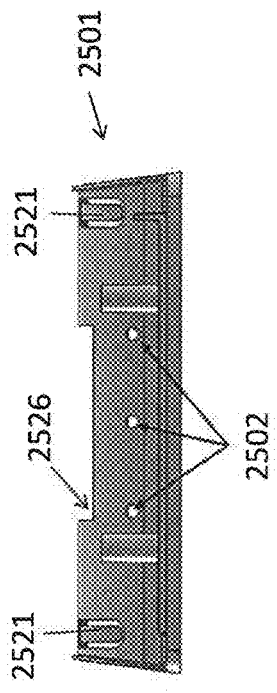
Figure 25C:
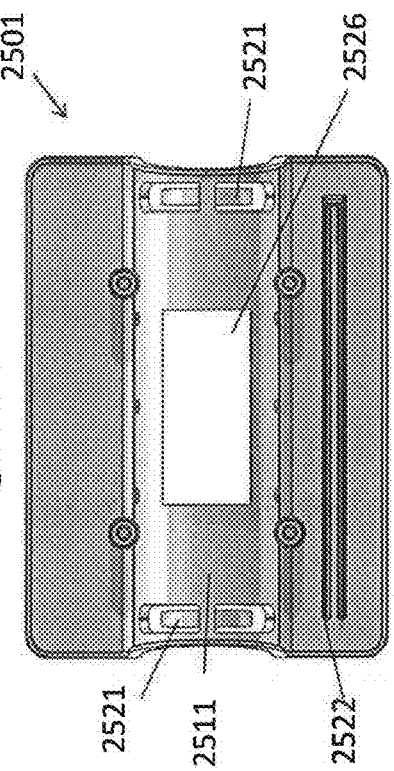

FIGS. 25A-25D show a mounting portion of a housing for a sensor cradle in accordance with example implementations. FIG. 25A provides a side view of mounting portion 2501. FIG. 25B provides an end view of the mounting portion 2501. FIG. 25C provides a top view of the mounting portion 2501. FIG. 25D provides a perspective view of the mounting portion 2501. The mounting portion 2501 includes a curved pipe interface 2511 and may include alignment tabs 2521 positioned in the pipe interface 2511. The mounting portion 2501 may include apertures 2502 for receiving a wedge as will be discussed further herein for aligning and engaging a pipe. The mounting portion 2501 includes an opening 2526 for receiving a sensor cradle. The mounting portion 2501 may also include a channel 2522 for locating and retaining a printed circuit board (used for power, control, and communication with the sensors).

Figure 26:
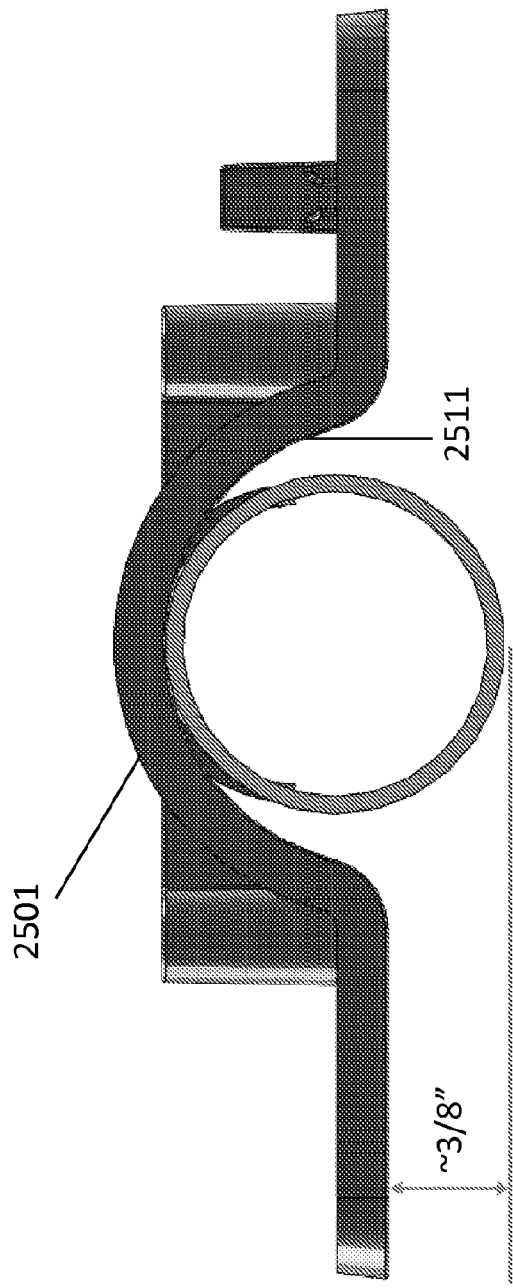
FIG. 26 is an end view of the mounting portion of FIGS. 25A-25D mounted on a pipe in accordance with example implementations.

FIG. 26 is an end view of the mounting portion of FIGS. 25A-25D mounted on a pipe in accordance with example implementations. The pipe interface 2511 of the mounting portion 2501 has a depth that permits a ¾ inch pipe to extend approximately ⅜ of inch from a surface of the mounting portion 2501. In cases when a pipe or conduit may be flush mounted against a wall or other solid structure, this clearance allows the transducer assembly to be installed with no interference with the wall or solid structure. The pipe is engaged by alignment tabs 2521.

Figure 27:
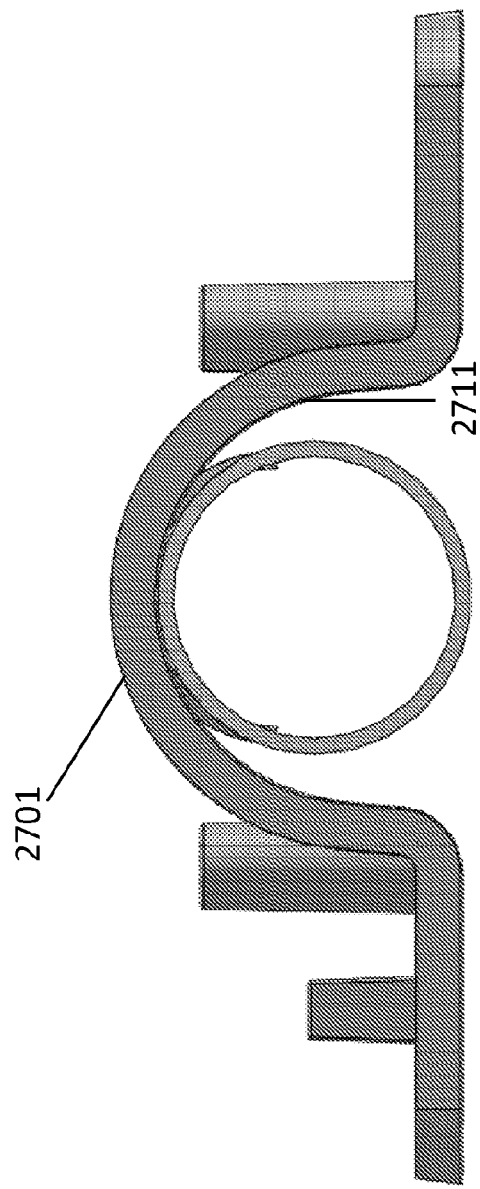
FIG. 27 is an end view of an extending mounting portion mounted on a pipe in accordance with example implementations.

FIG. 27 is an end view of an extended mounting portion mounted on a pipe in accordance with example implementations. The pipe interface 2711 of the mounting portion 2701 has a depth that permits a ¾ inch pipe to sit substantially flush with a surface of the mounting portion 2701. This allows the transducer assembly to be installed flush against a wall or solid structure with minimal interference with the wall or solid structure.

Figure 28B:
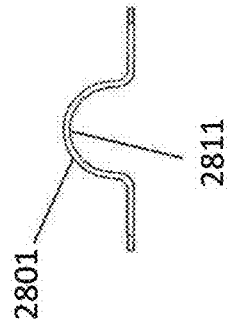
FIGS. 28A-28D show a mounting portion of a housing for a sensor cradle having clamping features in accordance with example implementations.
Figure 28D:
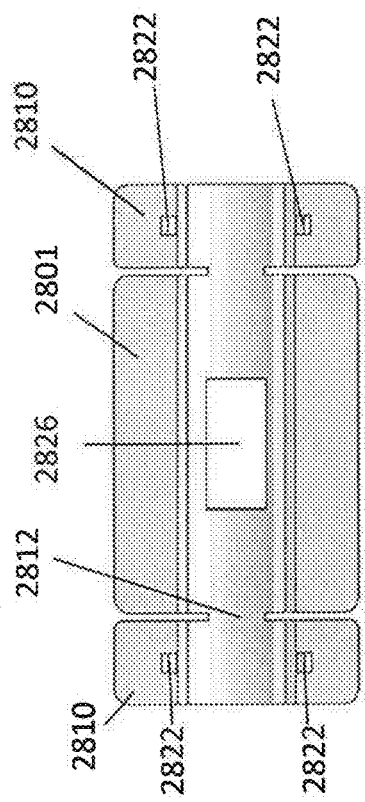
Figure 28A:
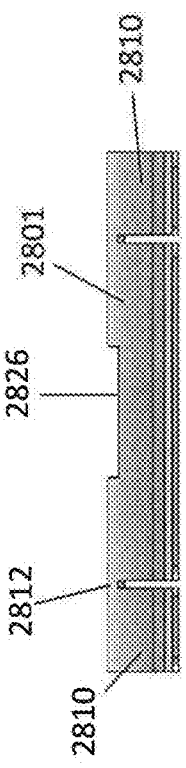
Figure 28C:
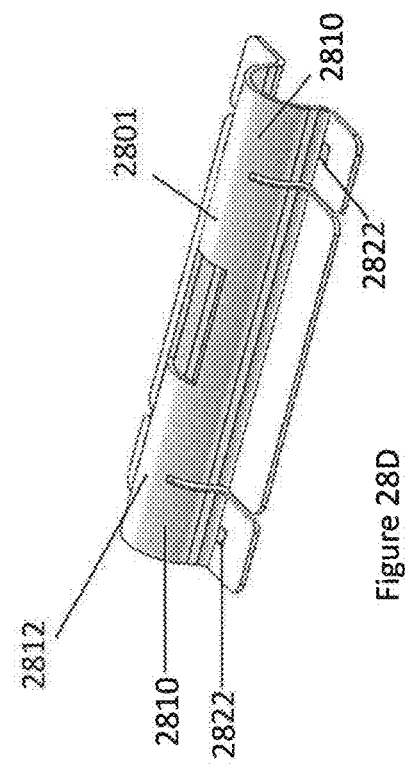

FIGS. 28A-28D show a mounting portion of a housing for a sensor cradle having clamping features in accordance with example implementations. FIG. 28A provides a side view of mounting portion 2801. FIG. 28B provides an end view of the mounting portion 2801. FIG. 28C provides a top view of the mounting portion 2801. FIG. 28D provides a perspective view of the mounting portion 2801. The mounting portion 2801 includes clamping features 2810 that extend from the mounting portion 2801. As shown, the clamping features 2810 may be coupled to the mounting portion 2801 via neck 2812 allowing the mounting portion 2801 additional flexibility when the clamping features 2810 are tightly coupled to a pipe or conduit. The clamping features 2810 include apertures 2822 for receiving a clamp or other coupling member therethrough. The mounting portion 2801 can include an opening 2826 configured to receive a sensor cradle in accordance with example implementations described herein. The mounting portion 2801 includes a curved interface 2811. The clamping features 2810 may be curved in a manner corresponding to the curved interface 2811 in accordance with various implementations.

Figure 29:
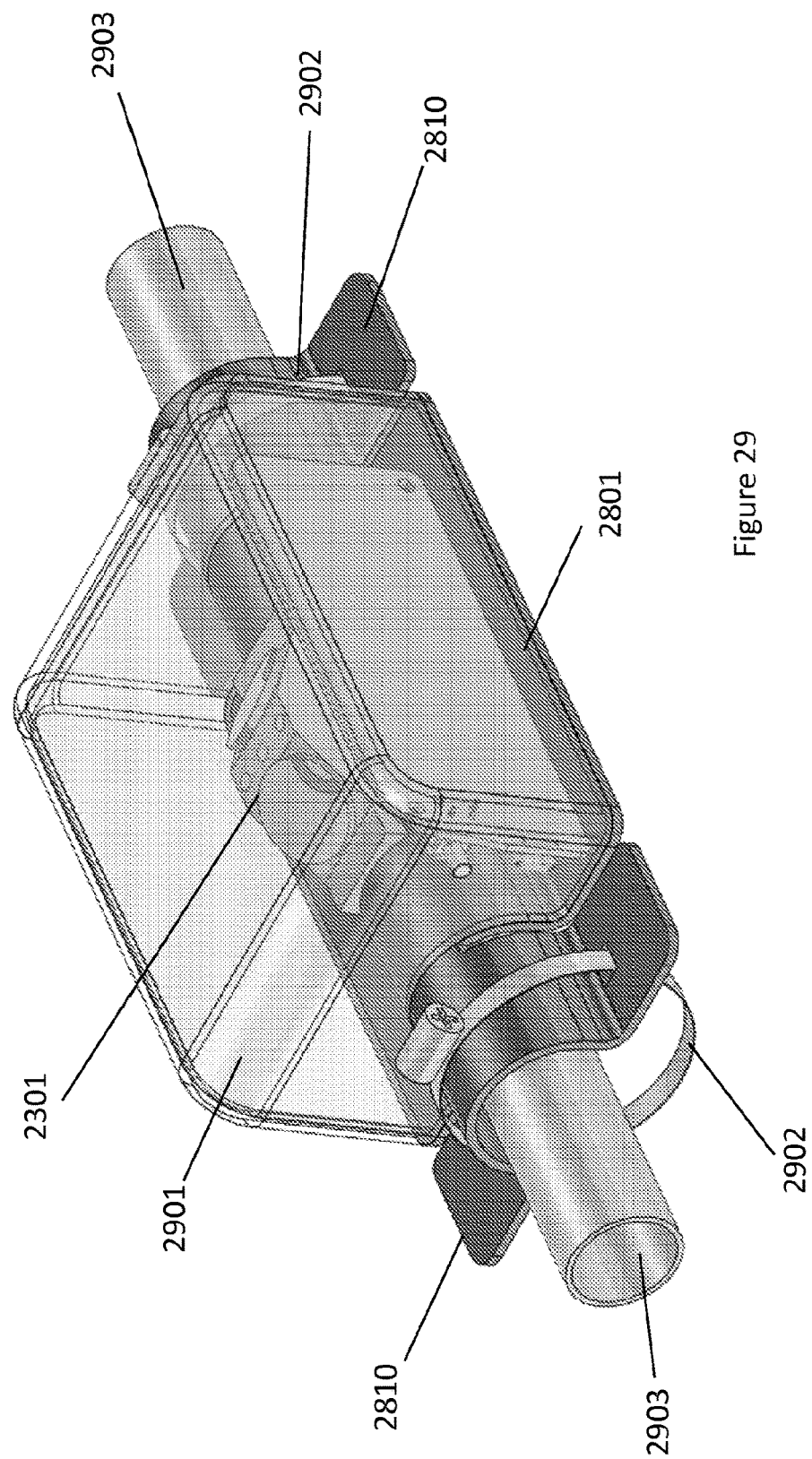
FIG. 29 provides a perspective semi-transparent view of a housing coupled to a mounting portion having clamping features engaged with clamps on a pipe in accordance with example implementations.

FIG. 29 provides a perspective semi-transparent view of a housing coupled to a mounting portion having clamping features engaged with clamps on a pipe in accordance with exemplary embodiments. The mounting portion 2801 is coupled to a housing cover 2901 to house a sensor cradle, such as sensor cradle 2301. The clamping features 2810 are engaged with clamps 2902 that extend through apertures 2822 to clamp pipe 2903 to mounting portion 2801.

Figure 30A:
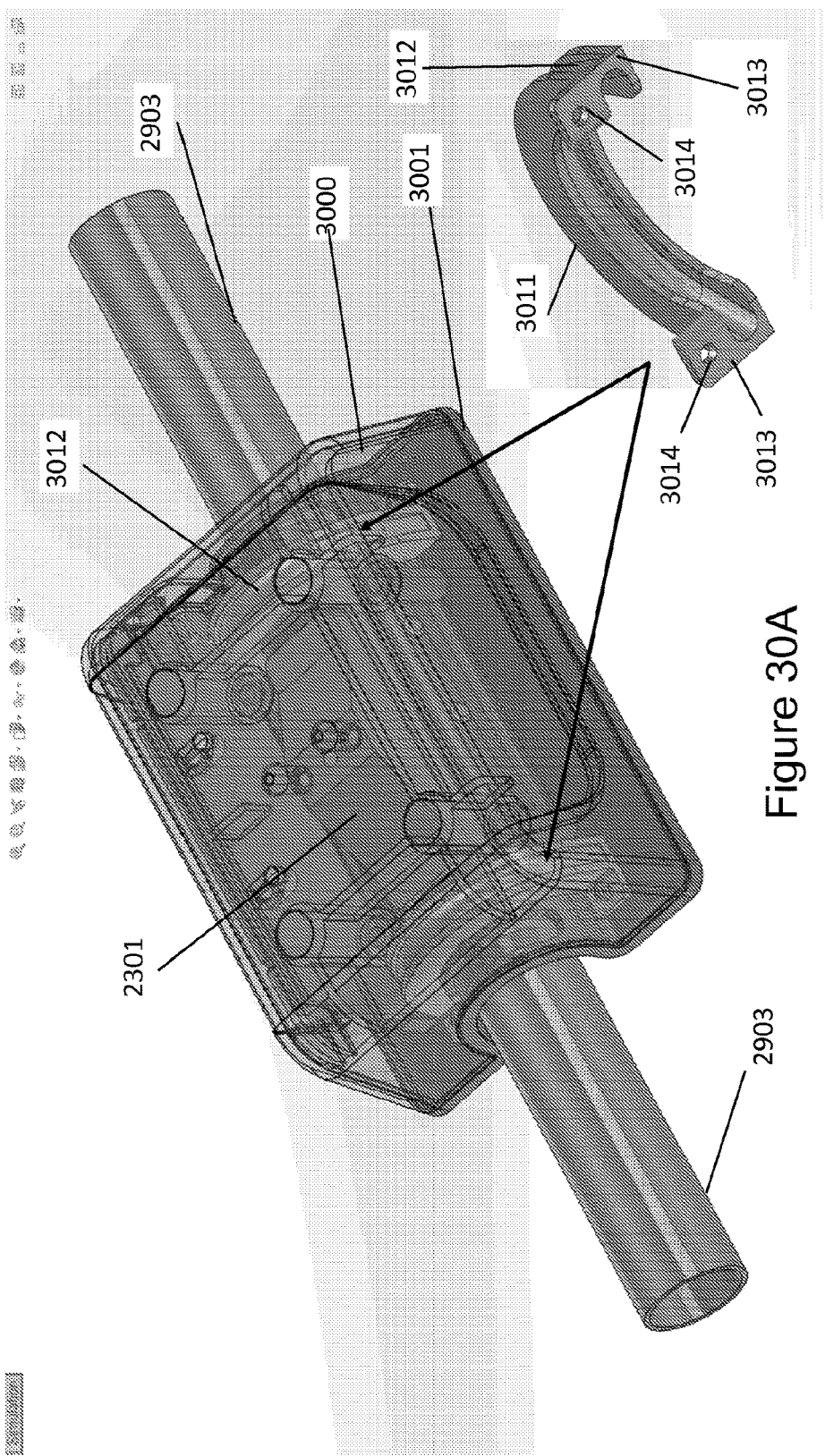
FIGS. 30A and 30B provides a perspective semi-transparent view of a housing coupled to a mounting portion having internal cable tie guide features engaged with cable ties on a pipe in accordance with example implementations.
Figure 30B:
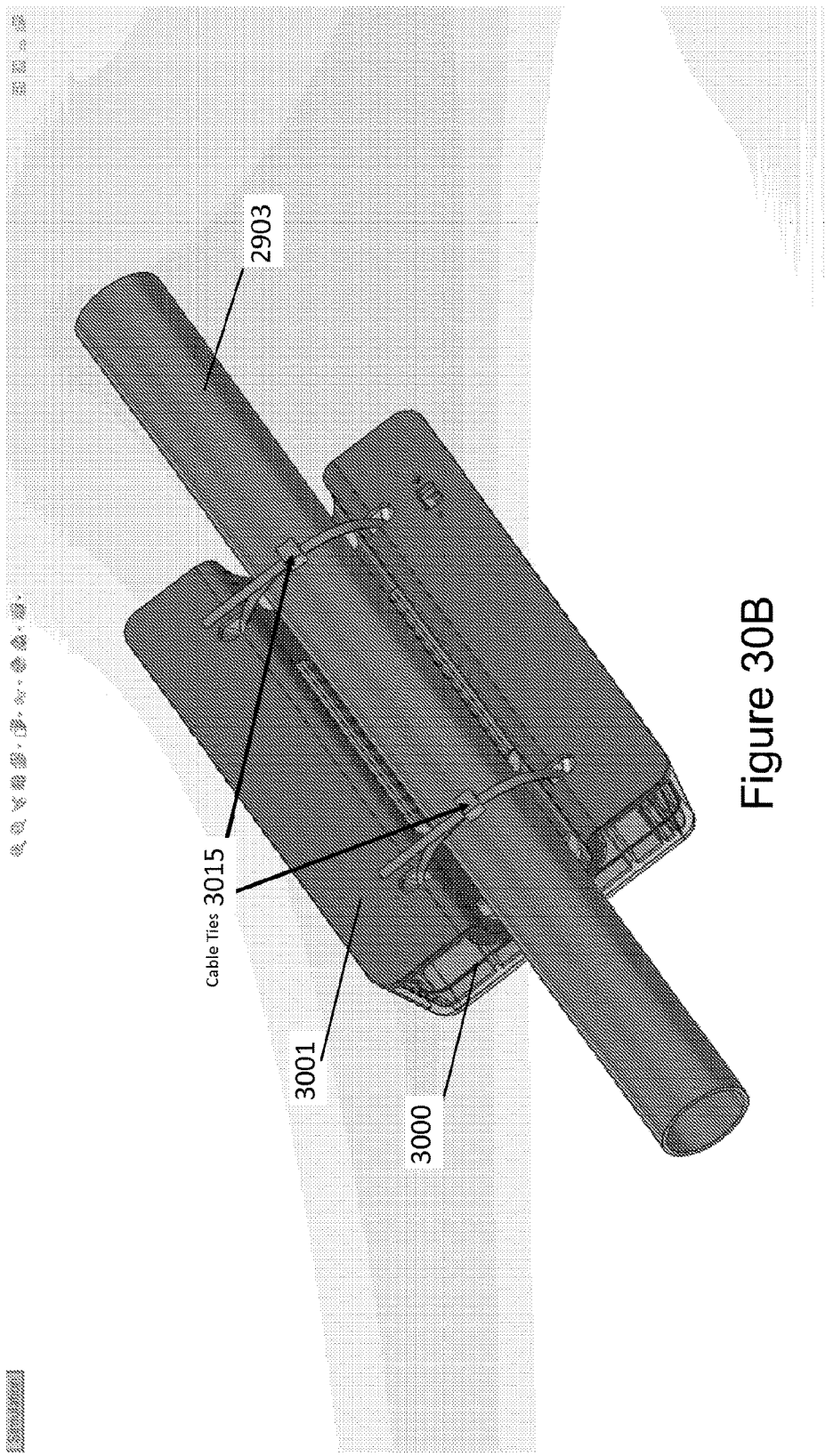

FIGS. 30A and 30B provide a top and bottom perspective views of a housing coupled to a mounting portion having internal cable tie guide features engaged with cable ties on a pipe in accordance with example implementations. The housing cover 3000 and the mounting portion 3001, in addition to housing a sensor cradle 2301, house cable tie guides 3011. The cable tie guides 3011 are structure in a semi-circular manner to conform to the pipe interface of the mounting portion 3001. The cable tie guides 3011 include a channel 3012 for receiving a coupling component such as a cable guide. The cable tie guides 3011 include footings 3013 that includes fastening apertures 3014 for securing the cable tie guides to the mounting portion 3001. The channel 3012 of the cable tie guides 3011 is configured for alignment with apertures in the mounting portion 3001 so that cable ties 3015 can extend through the mounting portion, out of the housing and around the pipe 2903.

Figure 31:
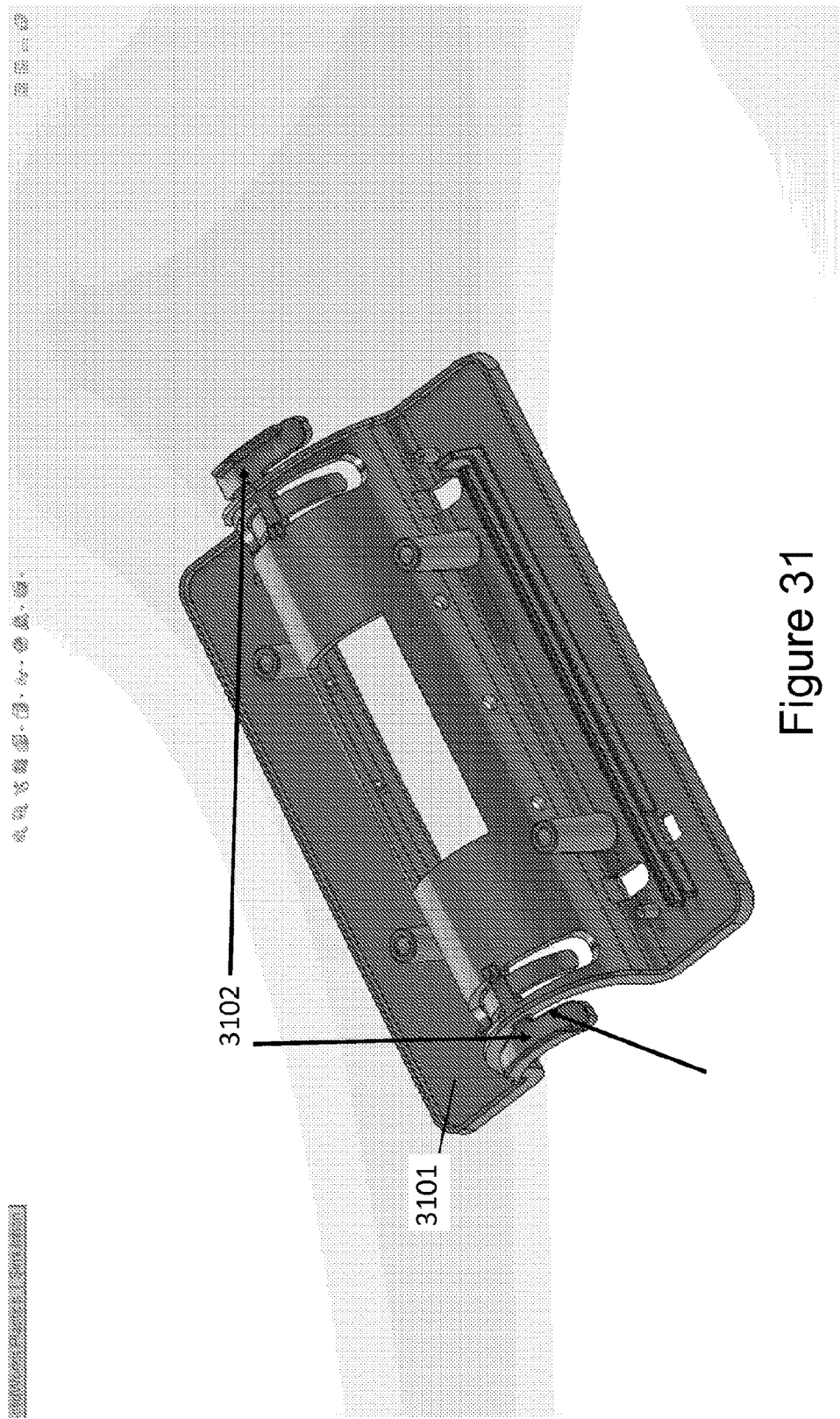
FIG. 31 shows another mounting portion of a housing for a sensor cradle having external clamping features in accordance with example implementations.

FIG. 31 shows another mounting portion of a housing for a sensor cradle having external clamping features in accordance with example implementations. The clamping features 3102 extending from mounting portion 3101 are configured to extend outside of a cover and housing for housing a sensor cradle. The clamping features 3102 are curved to conform to a pipe disposed therein and include a flange for maintain a coupling component such as tie, clamp, or other fastener therein.

Figure 32:
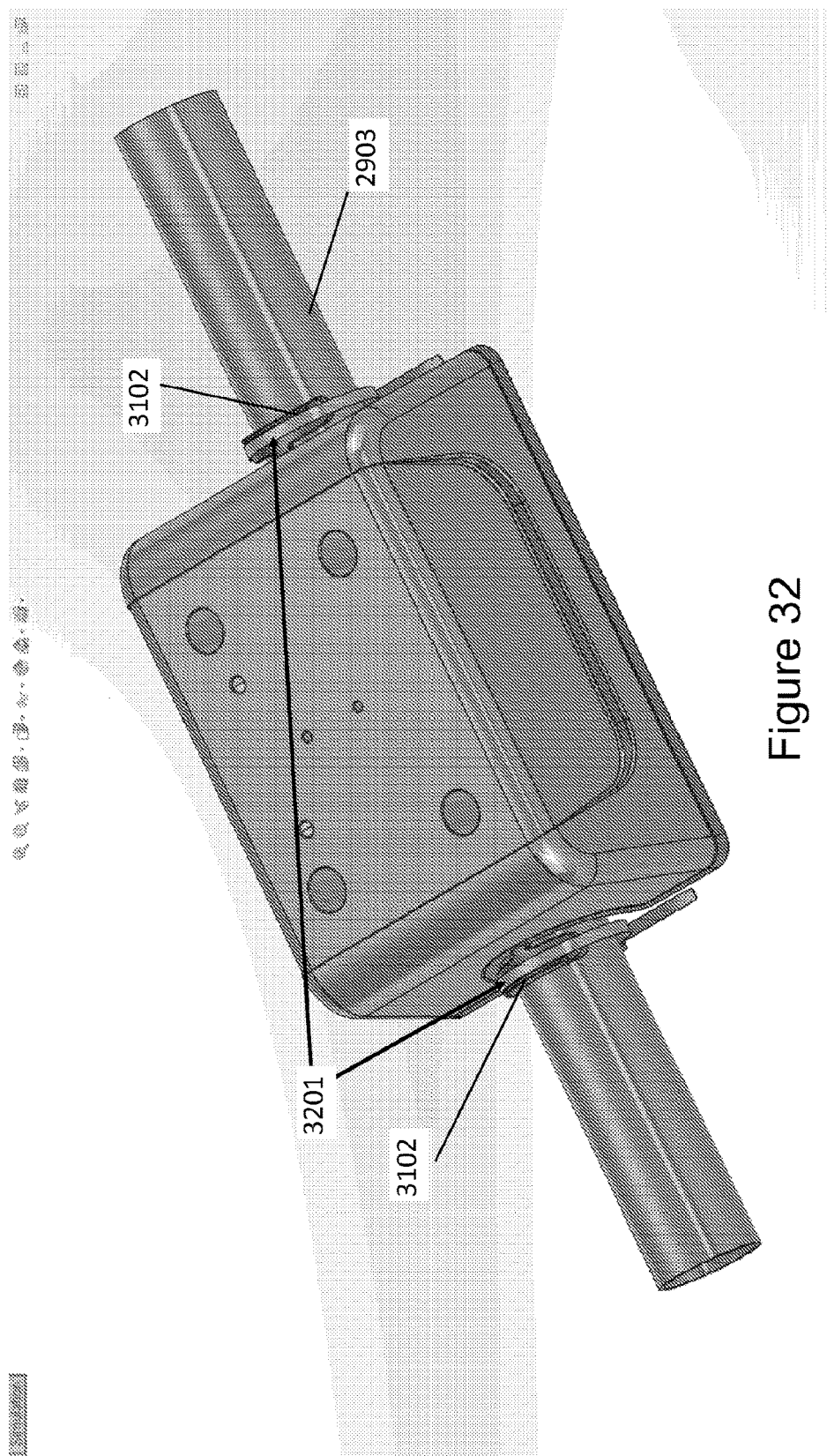
FIG. 32 provides a perspective view of a housing coupled to the mounting portion of FIG. 31 and having clamping features engaged with ties on a pipe in accordance with example implementations.

FIG. 32 provides a perspective view of a housing coupled to the mounting portion of FIG. 31 and having clamping features 3102 engaged with ties 3201 on a pipe 2903 in accordance with example implementations.

Figure 33B:
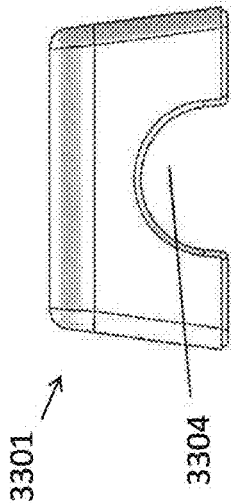
FIGS. 33A-33D show a housing cover in accordance with example implementations.
Figure 33A:
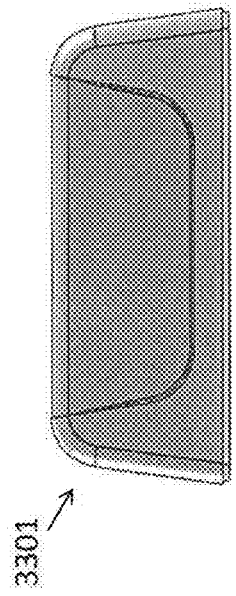
Figure 33D:
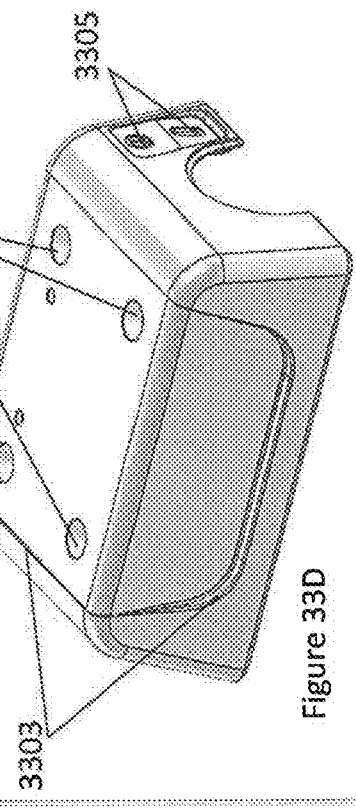
Figure 33C:
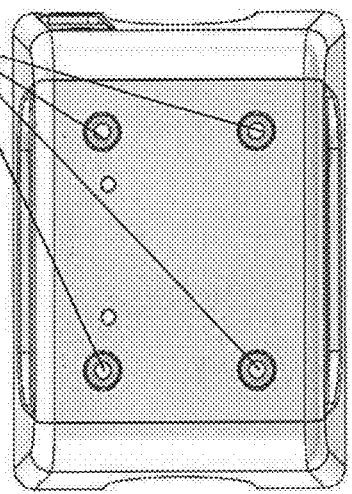

FIGS. 33A-33D show a housing cover in accordance with example implementations. FIG. 33A provides a side view of housing cover 3301. FIG. 33B provides an end view of the housing cover 3301. FIG. 33C provides a top view of the housing cover 3301. FIG. 33D provides a perspective view of the housing cover 3301. The housing cover may include one or more apertures 3302 for receiving fasteners, such as screws configured to connect housing cover 3301 to a mounting base portion. The apertures may be counter-bored and may be disposed in a recessed region 3303 configured to receive a cover for hiding the fasteners. The housing cover 3301 includes an arch 3304 for receiving a conduit such as pipe 2903 there through. The housing cover 3301 may include one or more ports 3305 configured for receiving an electrical connector to connect to electrical components housed with cover 3301.

Figure 34:
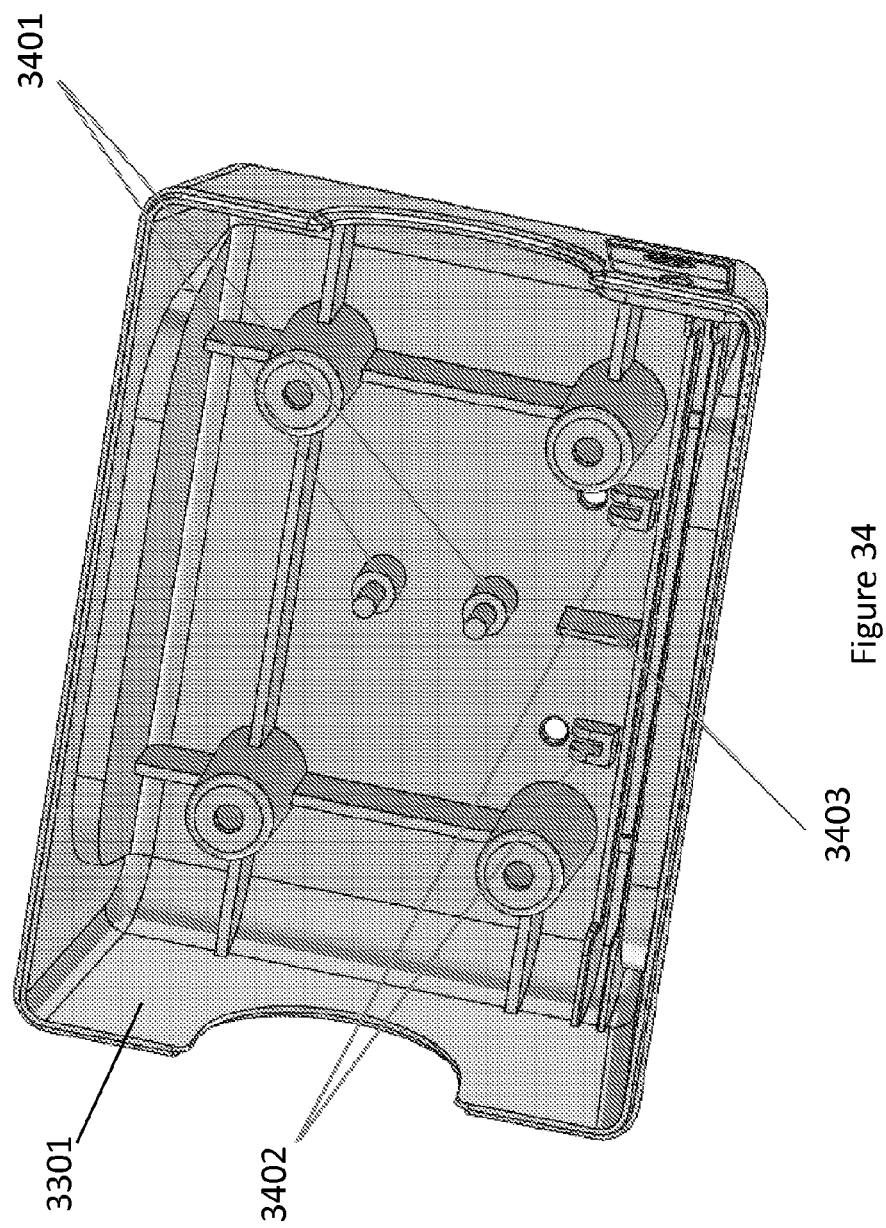
FIG. 34 shows the inside of a housing cover in accordance with example implementations.

FIG. 34 shows the inside of a housing cover in accordance with example implementations. Housing cover 3301 is configured for coupling with a sensor cradle, such as sensor cradle 2301. Housing cover 3301 includes locating posts 3401 configured to engage one or more alignment bores, such as alignment bores 2304 for alignment of the trapezoidal sensor cradle 2301 with the housing components such as a housing cover. The housing cover 3301 may also include light-guide retainers 3402 for seating indicator lights, such as LED (light emitting diode) indicator lights, therein and may also include a wall 3403 disposed therebetween to prevent the light from a first indicator light from interfering with light from a second indicator light. In example implementations, the indicator lights may be implemented for installation confirmation in conjunction with electronics that control the transducers and assess signal quality. In some implementations, proper installation of the sensor cradle may complete a circuit that generate a signal whose strength can be evaluated by the control electronics. The control electronics in turn can enable various blinking or stable patterns or combinations of permits power to be transmitted to the LED indicator lights to confirm that the sensor cradle was properly installed. In example implementations, the LED indicator lights are configured to light up in response to the sensor cradle being properly aligned with respect to a pipe that it is coupled to.

Figure 35:
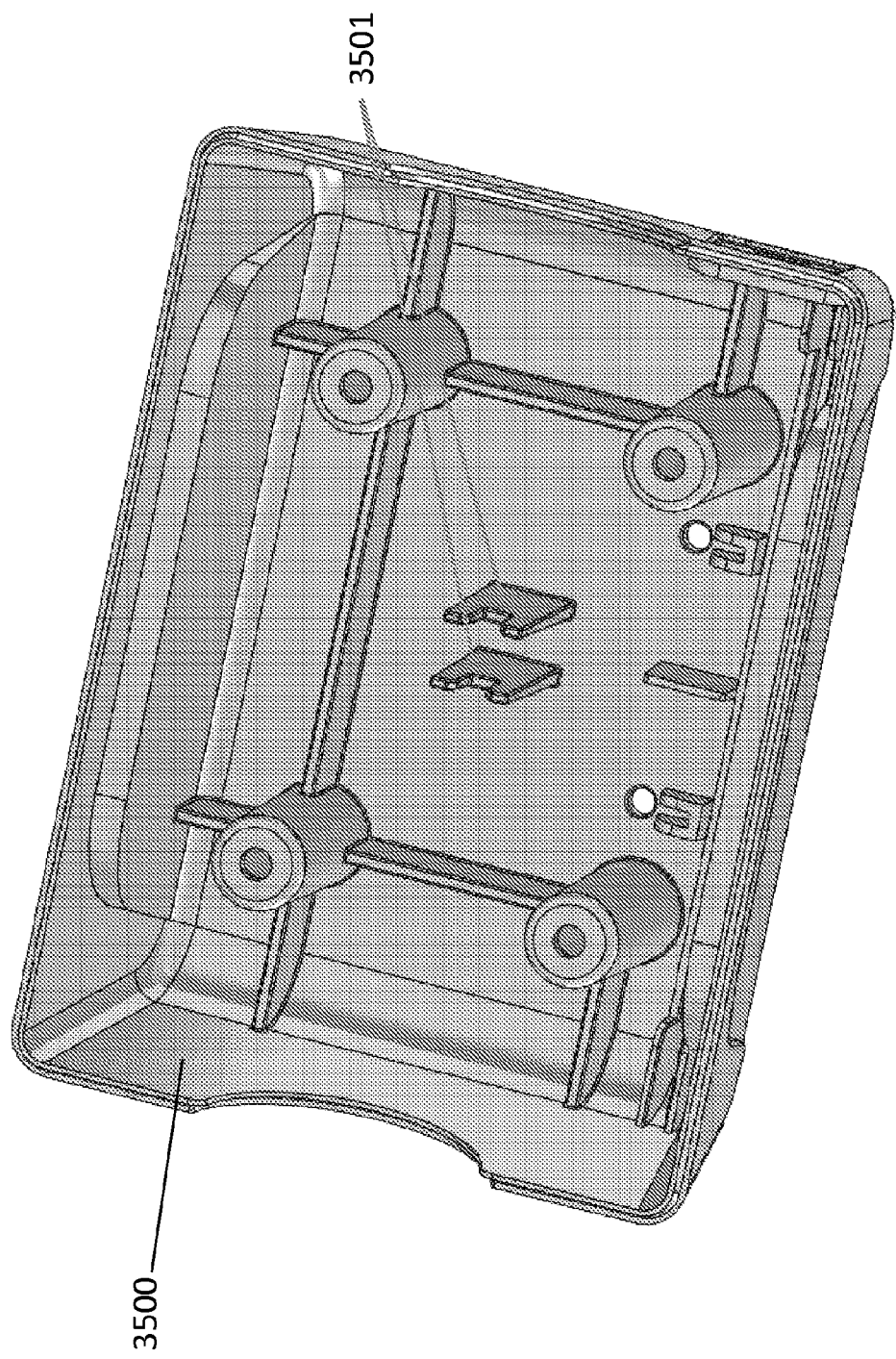
FIG. 35 shows the inside of another housing cover in accordance with example implementations.
Figure 36B:
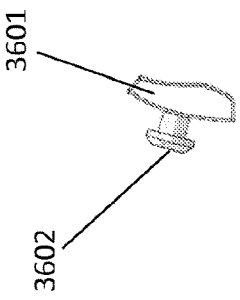
FIGS. 36A-36D show a wedge for use with a mounting portion in accordance with example implementations.
Figure 36D:
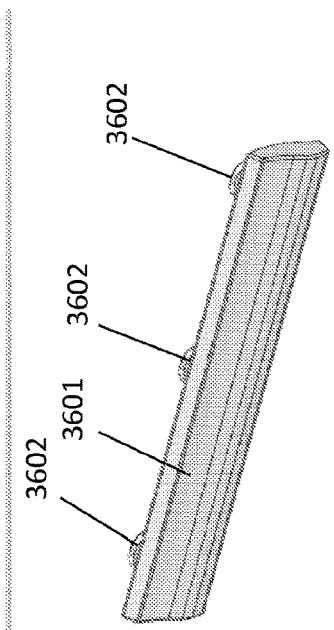
Figure 36A:
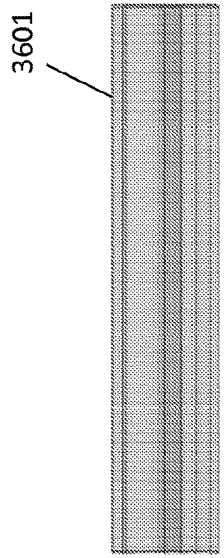
Figure 36C:
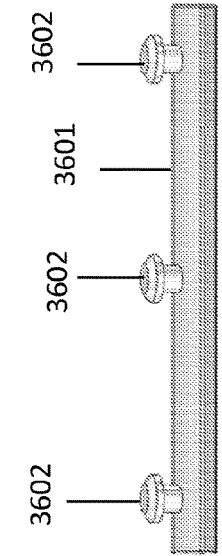

FIG. 35 shows the inside of another housing cover in accordance with example implementations. Housing cover 3500 includes locating posts 3501 configured to engage a sensor cradle.

FIG. 36 shows a wedge for use with a mounting portion in accordance with example implementations. FIG. 36A provides a front view of wedge 3601. FIG. 36B provides an end view of the wedge 3601. FIG. 36C provides a top view of the wedge 3601. FIG. 36D provides a perspective view of the wedge 3601. Wedge 3601 may be composed of an elastomeric material and helps keeps a sensor cradle aligned with a pipe, particularly pipes that are smaller than the pipe interface of a mounting portion coupled to a sensor cradle. The wedge 3601 may include a plurality of stems 3602 for engaging apertures in a mounting portion.

FIG. 37 shows the wedge of FIG. 36 coupled to a mounting portion in accordance with example implementations. The wedge 3601 is engaged with the mounting portion 2501 via stems 3602.

FIG. 38 provides an end view of a sensor cradle housing assembly coupled to a pipe in accordance with example implementations. The wedge 3601 is engaged with the mounting portion 2501 such that the wedge 3601 interfaces with pipe 2903.

Figure 39:
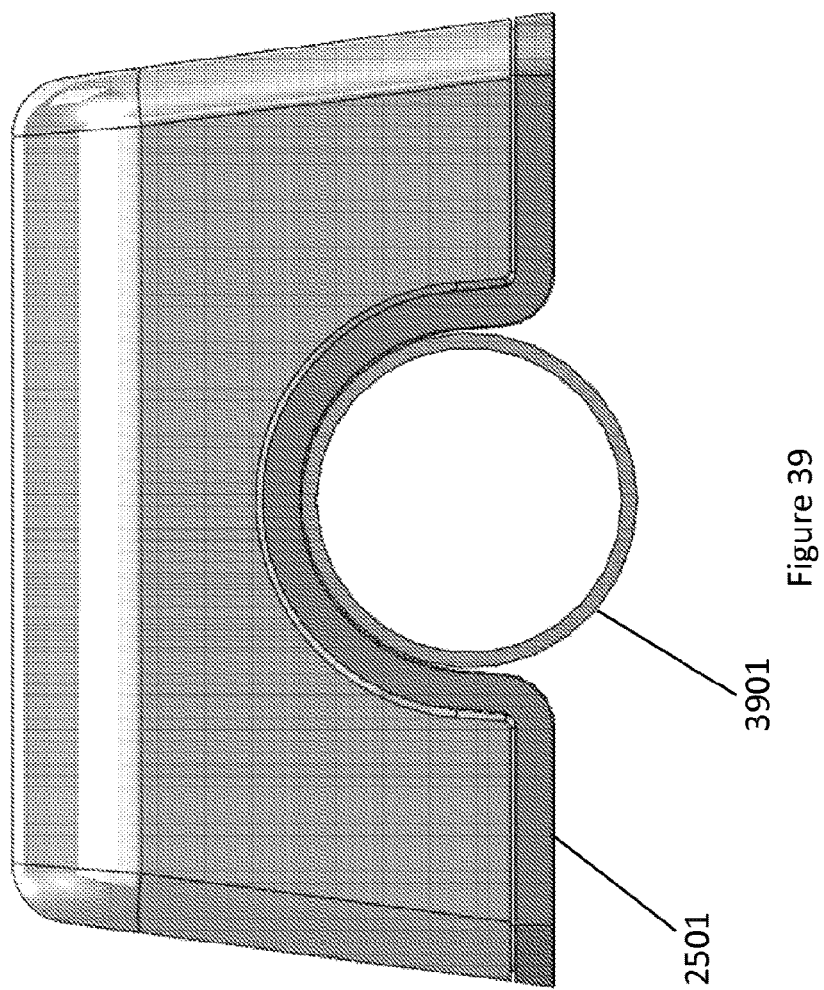
FIG. 39 provides an end view of a sensor cradle housing assembly coupled to another pipe in accordance with example implementations.

FIG. 39 provides an end view of a sensor cradle housing assembly coupled to another pipe in accordance with example implementations. As demonstrated in FIG. 39, if a larger pipe such as pipe 3901 is disposed in the mounting portion 2501, the wedge 3601 may be removed from the mounting portion.

Figure 40:
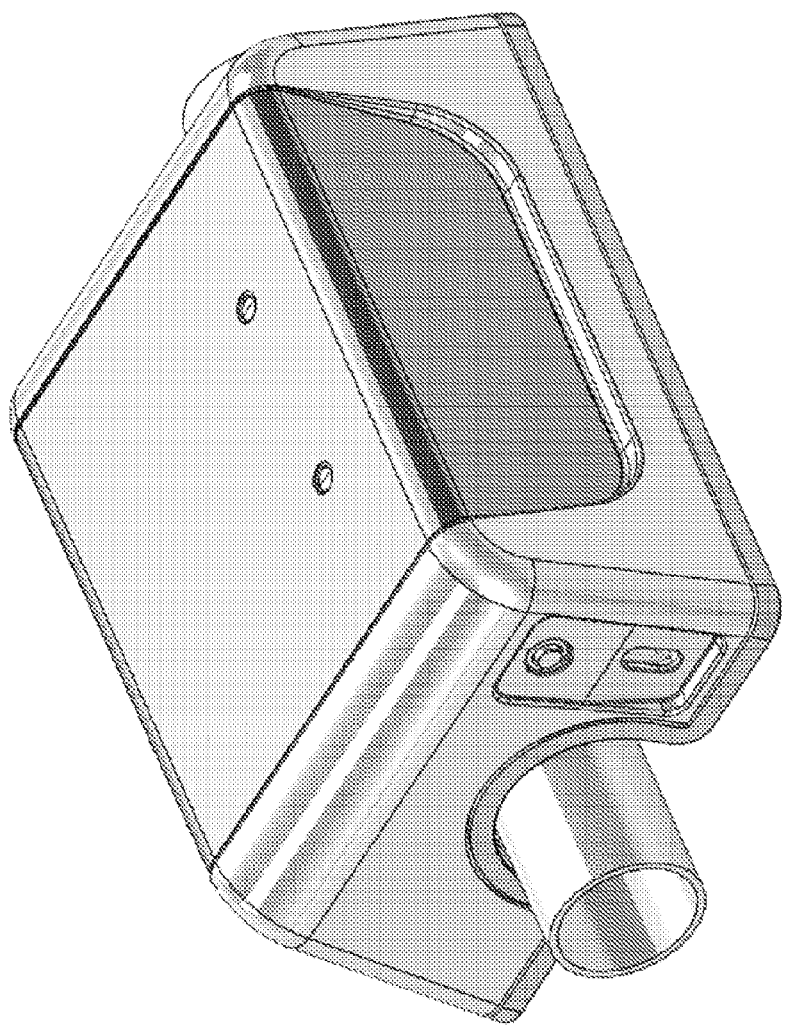
FIG. 40 provides a perspective view of a sensor cradle housing assembly coupled to a pipe in accordance with example implementations.

FIG. 40 provides a perspective view of a sensor cradle housing assembly coupled to a pipe 3901 in accordance with example implementations.

Figure 41B:
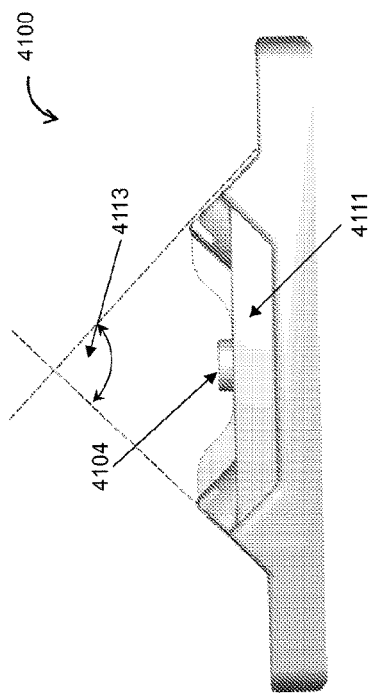
FIGS. 41A-41H illustrate another sensor cradle including separable wave-guides.
Figure 41D:
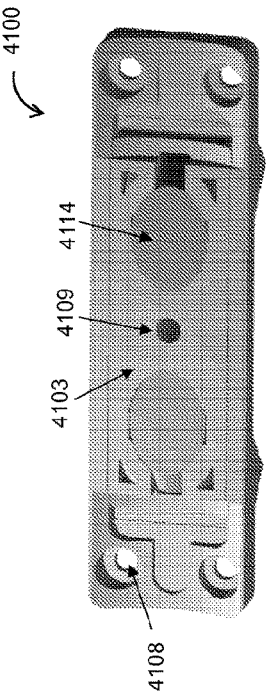
Figure 41A:
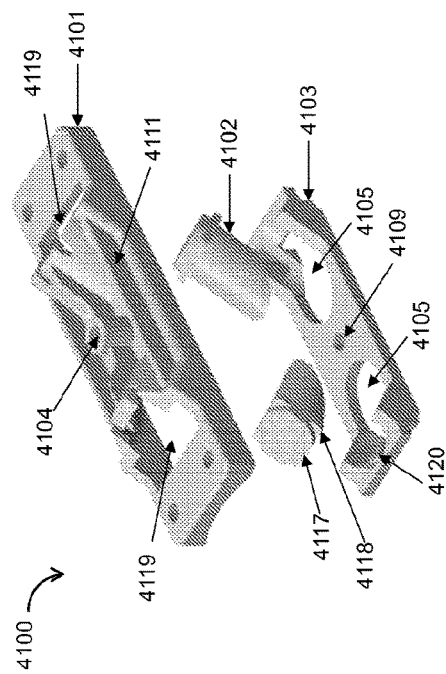
Figure 41C:
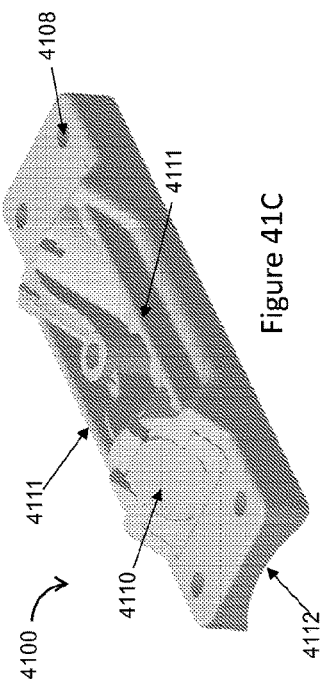
Figure 41F:
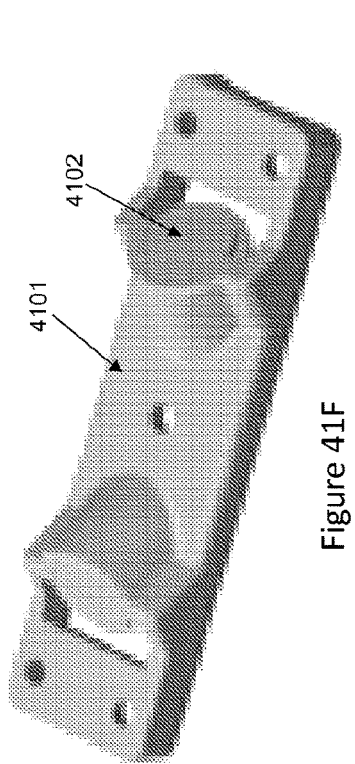
Figure 41H:
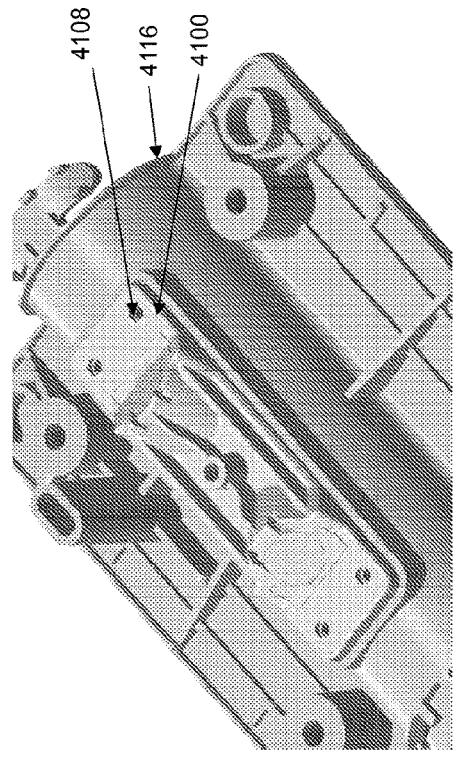
Figure 41E:
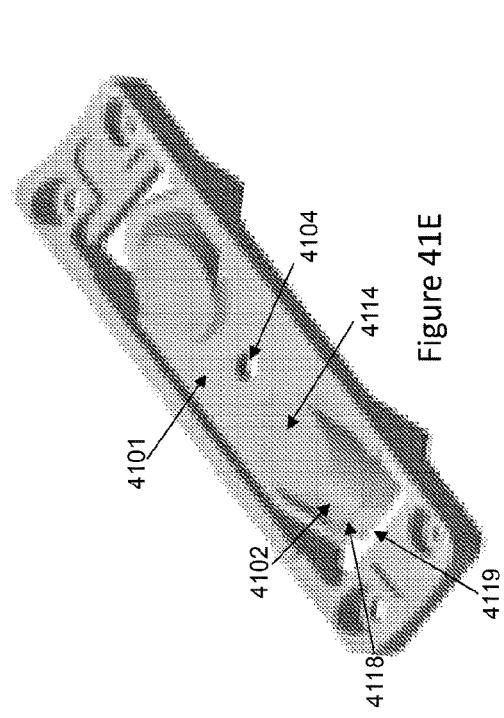
Figure 41G:
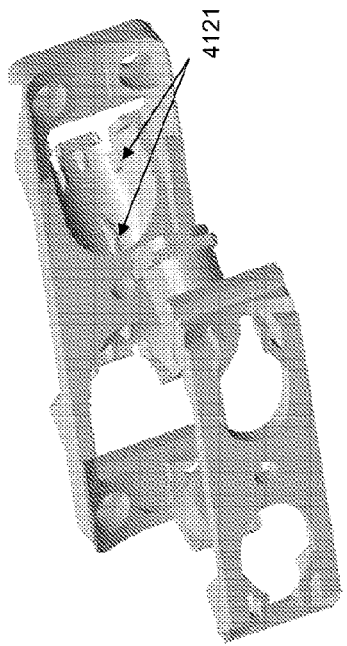

FIGS. 41A-41H show diagrams illustrating another sensor cradle 4100. The sensor cradle 4100 includes a top shell (or a first shell) 4101, a bottom shell (or a second shell) 4103 and a pair of waveguides 4102. FIGS. 41A and 41G show two different view of the top shell 4101, the bottom shell 4103 and the waveguides 4102 in a non-assembled mode. FIGS. 41B-41D show different views of the assembled sensor cradle 4100. FIGS. 41E and 41F show bottom and top views, respectively, of the top shell 4101 with the waveguides mounted thereon. FIG. 41H shows a diagram illustrating the sensor cradle 4100 mounted on a mounting device 4116.

The sensor cradle design illustrated in FIGS. 41A-41H allows for separate, easy and cheap manufacturing of the top shell 4101, the bottom shell 4103 and the waveguides 4102. For instance, the top shell 4101, the bottom shell 4103 and the waveguides 4102 can be manufactured using injection molding and possible using different materials. Also, the design allows for separate assembly of transducers to the waveguides 4102 (for instance using an epoxy or an adhesive material) and then installing the waveguides 4102 (with the transducers) with the top and bottom shells 4101 and 4103 to form the assembled sensor cradle 4100.

The top shell 4101 can include openings 4119 for housing the waveguides 4102. The upper shell 4101 can include a bore hole 4104 for housing an auxiliary component such as a thermistor or another sensor. The top shell 4101 can include one or more structures 4111 (such as a wall-like structure) to increase the rigidity or strength of the top shell 4101. The top shell 4101 can include openings 4108 for housing fasteners (such as screws) used to couple the assembled sensor cradle 4100 to a mounting device such as mounting device 4116. In some implementations, other coupling features such as snap features or an epoxy can be employed to couple the assembled sensor cradle 4100 to the mounting device 4116. The top shell 4101 can include a curved interface 4112 arranged to align the assembled sensor cradle 4100 with the mounting device 4116 by engaging a matching surface of the mounting device 4116 (or the pipe wall).

The bottom shell 4103 can include openings 4105. Each opening 4105 is arranged to house at least a portion of a transducer and can be aligned with a respective opening 4119 (when the top shell 4101 and bottom shell 4103 are assembled together) along an axis of a respective waveguide 4102. The bottom shell 4103 can include a bore hole 4109 arranged to be aligned with the borehole 4104 (when the top shell 4101 and bottom shell 4103 are assembled together). The top shell 4101 and the bottom shell 4103 can include snap features (not shown in FIGS. 41A-41H) for coupling the top and bottom shells 4101 and 4103 together. For instance, the top shell 4101 can include snap feature(s) along one or more respective bottom edges and the bottom shell 4103 can include snap feature(s) along one or more respective top-side edges. The snap features in the top and bottom shells can be arranged to match (such as to be aligned) and allow both shells 4101 and 4103 to snap to each other. In some implementations, the top and bottom shells 4101 and 4103 can be coupled to each other using fasteners or other coupling features.

The waveguides 4102 are arranged to be positioned within the openings 4119 and 4105. Each waveguide 4102 can include tabs (such as tabs triangular tabs) 4118. Each tab 4118 can be arranged to engage respective grove structures (or other structures) in the top shell 4101 and/or the bottom shell 4103. As such, the tabs 4118 prevent the respective waveguide 4102 from moving along the axis of the openings 4119 and 4105 (e.g., up and down) when assembled with top and bottom shells 4101 and 4103. Each waveguide 4102 can include one or more truncated edges 4117 arranged to prevent the waveguide from rotating when assembled with top and bottom shells 4101 and 4103. The truncated edges 4117 can be arranged to engage a matching surface 4120 in the bottom shell 4103. While the waveguide cross section has a circular shape (along at least a portion of the respective axis), the cross section can have other shapes (other than circular) such as square, rectangle, hexagon, octagon or other shapes. In some implementations, keyed structures can be employed (for instance instead of the truncated edges 4117) to prevent rotational motion of the waveguides when assembled with top and bottom shells 4101 and 4103.

The surfaces 4110 of the waveguides 4102 are arranged for seating and maintaining the transducers. The surfaces 4110 (and the transducers when coupled to the waveguides 4102) can be arranged substantially orthogonal (at an angle 4113) with respect to each other when the waveguides 4102 are assembled with the top and bottom shells 4101 and 4103. That is, the angle 4113 can be between 75° and 90°, 80° and 90°, between 85° and 90° or other range of angles with angle values in proximity to 90°. The transducers can be fixed or coupled to the surfaces 4110 through an epoxy or an adhesive. The surfaces 4114 of the waveguides 4102 are arranged to face the mounting device and the conduit (such as a pipe) through which fluid is flowing. In some implementations, the surfaces 4114 can be configured to be aligned with the bottom surface of the bottom shell 4103. For instance, the openings 4119 and 4105 and the waveguides 4102 can be arranged (e.g., respective sizes, orientations and geometries can be configured) such that the surfaces 4114 are aligned with the bottom surface of the bottom shell 4103.

As illustrated in FIG. 41G, the top shell 4101 can include standoff tabs 4121 arranged in the walls of the openings 4119 to substantially isolate the waveguides 4102 from the top shell 4101 (and the bottom shell 4103) by introducing an air gap in between. That is, the standoff tabs 4121 allow for reducing the contact surface areas between the waveguides 4102 and the shells 4101 and 4103 and, therefore, limiting signal propagation into the shells 4101 and 4103. Signal propagation through the shells 4101 and 4103 can result in receiving at one transducer multiple echoes (or distinct delayed versions) of a transmitted signal by another transducer. The multiple echoes can be associated with different thermal properties (e.g., thermal properties of the waveguides 4102 can be different from those of the shells 4101 and 4103) and therefore can negatively impact any estimates of fluid flow properties based on such received signals. In some implementations, the waveguides 410 and the shells 4101 and 4103 can be manufactured from different materials to reduce signal propagation into the shells 4101 and 4103 and reduce signal propagation paths. As such, and the sensor cradle 4100 can have improved thermal stability. In some implementations, the standoff tabs 4121 as well as different materials for the waveguides 4102 and the shells 4101 and 4103 can be employed.

In some implementations, the waveguides can be manufactured from Ultem. Ultem has a relatively low signal refraction index with copper and plastic. As such, using Ultem allows for reduced signal refraction at the interface between the waveguides 4102 and the conduit (such as pipe). In some implementations, the waveguides 4102 can be manufactured from ceramic, plastic, metal or other materials. In some implementations, the waveguides material can vary, for instance, based on pipe material. The shells 4101 and 4103 can be manufactured from plastic (such as PVC, CPC or PEX), metal, ceramic or other materials.

FIG. 41H shows a mounting device 4116 for coupling the sensor cradle 4100 to a conduit (such as a pipe). The mounting device can include an opening for housing the sensor cradle 4100. The sensor cradle 4100 can be employed with any of the mounting devices described in this disclosure. Coupling the sensor cradle 4100 to the mounting device 4116 provides mechanical stability to the sensor cradle 4100 as the top and bottom shells are pushed towards each other. The sensor cradle 4100 can be assembled by installing the waveguides 4102 into the top shell 4101 and then coupling the top shell 4101 (with the waveguides 4102) to the bottom shell 4103.

Figure 42B:
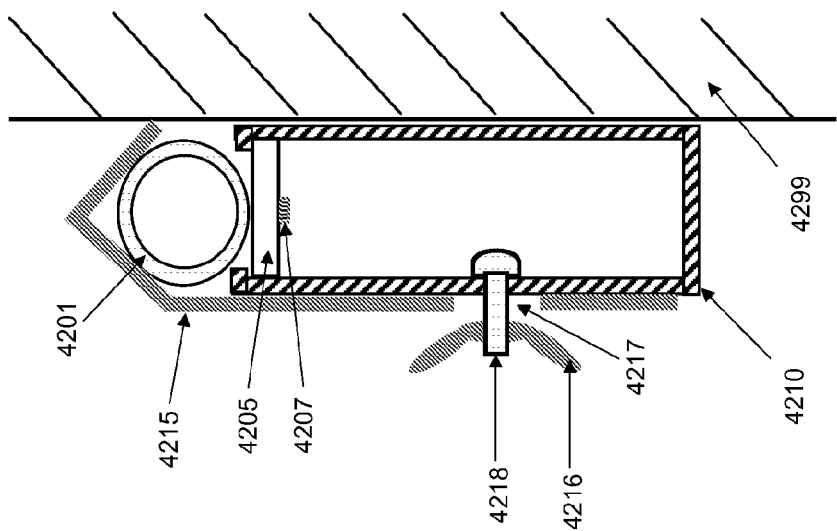
FIGS. 42A and 42B illustrate a hook-based mechanism for mounting a sensor assembly to a conduit.
Figure 42A:
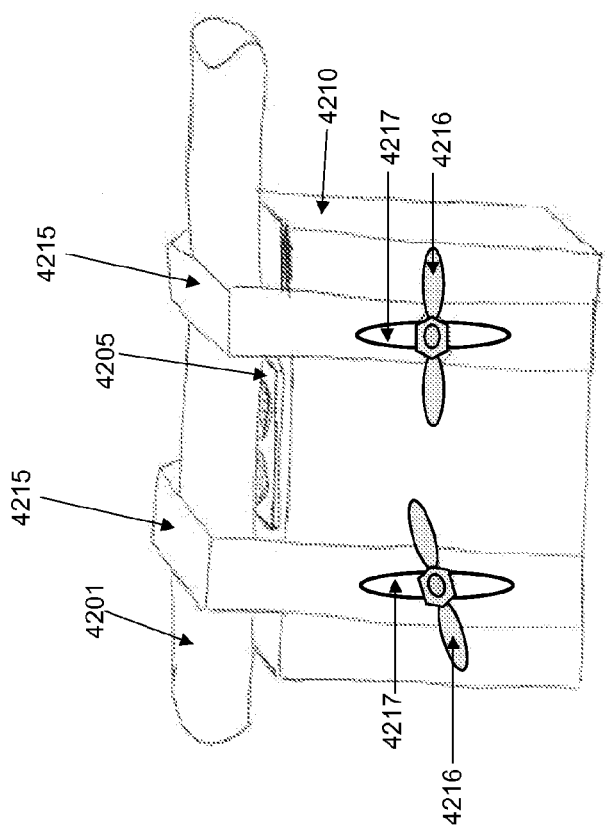

FIGS. 42A and 42B illustrate a hook-based mechanism for mounting a sensor assembly to a conduit. FIG. 42A shows a diagram illustrating a sensor assembly 4210 hooked to a pipe 4201 through hook elements 4215. The hook elements 4215 can be coupled to the sensor assembly 4210 through respective wing nuts 4216 (or types or nuts) and bolts 4218. That is, a bolt 4218 (penetrating through an opening within a wall of the sensor assembly 4210 and an opening 4217 of the hook element 4215) and a respective wing nut 4216 when fastened can couple the hook element 4215 to the sensor assembly 4210. The hook element 4215 can include an elongated opening 4217 allowing the hook element 4215 to exhibit translational motion when the wing nut 4216 is not fastened tight against the hook element 4215. The hook element 4215 is arranged to hook to the pipe 4201 through a respective angular (or curved) portion.

A user can slide the hook element(s) 4215 in a first direction to allow enough space for the pipe 4201 to engage the angular (or curved) portion(s) of the hook element(s) 4215. Once the angular (or curved) portion(s) of the hook element(s) 4215 is/are hooked around the pipe 4201, the user can push the hook element(s) 4215 in a direction opposite to the first direction and tighten the wing nut 4216. As a result, the pipe 4201 can be engaged by angular (or curved) portion(s) of the hook element(s) 4215 and the sensor assembly 4210 (or a sensor cradle 4205 mounted (or coupled) to the sensor assembly 4210. Accordingly, transducers 4207 installed (or fixed) within the sensor cradle 4205 can transmit waves to propagate in the pipe 4201. The hook elements 4215 can be viewed as being part of the sensor assembly 4210 or a separate component to be coupled to the sensor assembly 4210 to allow engaging the pipe 4201.

FIG. 42B shows a cross section of the drawing in FIG. 42A along a longitudinal axis of one of the openings 4217. Also, the sensor assembly 4210 is shown with respect to a wall 4299.

While FIG. 42A shows two hook elements 4215, the sensor assembly 4215 can be associated with a single hook element 4215 or more than two hook elements 4215. In some implementations, the hook element(s) 4215 can be coupled to the sensor assembly 4210 (or a wall thereof) through a spring or an elastic component allowing the hook element(s) 4215 to exhibit a translational motion along sensor assembly wall (for instance instead of having the opening 4217 and using the wing nut(s) 4216 and the bolt(s) 4218). The hook-based mechanism illustrated in FIGS. 42A and 42B can be employed with any of the sensor cradles or the sensor assemblies described in this disclosure.

As utilized herein, the terms "approximately," "about," "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described without restricting the scope of these features to the precise numerical ranges provided. Accordingly, these terms should be interpreted as indicating that insubstantial or inconsequential modifications or alterations of the subject matter described and are considered to be within the scope of the disclosure.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be noted that the orientation of various elements may differ according to other exemplary embodiments, and that such variations are intended to be encompassed by the present disclosure. It is recognized that features of the disclosed embodiments can be incorporated into other disclosed embodiments.

It is important to note that the constructions and arrangements of apparatuses or the components thereof as shown in the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present disclosure.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, describes techniques, or the like, this application controls.

While various inventive embodiments have been described and illustrated herein, those of ordinary skill in the art will readily envision a variety of other mechanisms and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, the technology described herein may be embodied as a method, of which at least one example has been provided. The acts performed as part of the method may be ordered in any suitable way unless otherwise specifically noted. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of"

"Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In any claims, as well as in the specification above, all transitional phrases such as "comprising," "including," "carrying," "having," "containing," "involving," "holding," "composed of," and the like are to be understood to be open-ended, i.e., to mean including but not limited to.

Any claims provided herein or appended hereto should not be read as limited to the described order or elements unless stated to that effect. It should be understood that various changes in form and detail may be made by one of ordinary skill in the art without departing from the spirit and scope of any appended claims. All implementations that come within the spirit and scope of any appended claims and equivalents thereto are claimed.

What is claimed is:

1. A sensor assembly for mounting transducers on a conduit to measure properties of fluid flowing in the conduit, the sensor assembly comprising:
    a sensor cradle including:
        seating structures for seating and maintaining ultrasonic transducers, the seating structures arranged to provide all orientation of the ultrasonic transducers with respect to each other to cause propagation of ultrasonic waves transmitted by the ultrasonic transducers into the conduit; and
        a physical structure defining a continuous waveguide between the seating structures within the sensor cradle, the waveguide guiding a reference ultrasonic signal to propagate within the sensor cradle between the ultrasonic transducers and the reference ultrasonic signal for we to compensate for effect of temperature variation on the ultrasonic waves propagating in the conduit; and
    a mounting device arranged to couple the sensor cradle to the conduit such that the transducers maintained at the sensor cradle are oriented to allow transmission of ultrasonic waves traversing the conduit.

2. The sensor assembly of claim 1, wherein the seating structures include recessed mounting surfaces for seating the ultrasonic transducers.

3. The sensor assembly of claim 2, wherein the recessed mounting surfaces are oriented substantially orthogonal to each other.

4. The sensor assembly of claim 2, wherein the ultrasonic transducers are coupled to the recessed mounting surfaces through an adhesive.

5. The sensor assembly of claim 1, wherein the sensor cradle includes a stabilizer track for engaging a cover portion of the mounting device.

6. The sensor assembly of claim 1, wherein the sensor cradle includes a bore hole for housing a thermistor.

7. The sensor assembly of claim 1, wherein the sensor cradle includes a curved interface for engaging the conduit.

8. The sensor assembly of claim 1, wherein the sensor cradle includes ledges capable of engaging a portion of the mounting device.

9. The sensor assembly of claim 1, wherein the seating structures include openings for housing the ultrasonic transducers.

10. The sensor assembly of claim 9, wherein the openings are arranged substantially orthogonal to each other.

11. The sensor assembly of claim 1, wherein the sensor cradle is composed of at least one of acrylic, polycarbonate, polysulfone, aluminum and copper.

12. The sensor assembly of claim 1, wherein the mounting device includes a mounting component for housing the sensor cradle and mounting the sensor cradle to the conduit.

13. The sensor assembly of claim 12, wherein the mounting component includes an opening for housing the sensor cradle.

14. The sensor assembly of claim 12, wherein the mounting component includes a curved interface arranged to engage the conduit.

15. The sensor assembly of claim 12, wherein the mounting component includes one or more clamping elements for coupling the mounting device to the conduit.

16. The sensor assembly of claim 15, wherein the one or more clamping elements are arranged to extend outside a cover component of the mounting device.

17. The sensor assembly of claim 12, wherein the mounting component is capable of being coupled to the conduit through one or more cables.

18. The sensor assembly of claim 17, wherein the mounting device includes one or more cable tie guides coupled to the mounting component.

19. The sensor assembly of claim 12, wherein the mounting device further includes a cover component capable of being Coupled to the mounting component.

20. The sensor assembly of claim 19, wherein the cover component includes one or more alignment posts for engaging a stabilizer track of the sensor cradle.

21. The sensor assembly of claim 20, wherein each alignment post includes a respective groove for engaging the stabilizer track of the sensor cradle.

22. The sensor assembly of claim 12, wherein the mounting component includes a hook element capable of coupling the sensor assembly to the conduit.

* * * * *